US012802805B2

(12) United States Patent
Narayana Reddy Gari et al.

(10) Patent No.: US 12,802,805 B2
(45) Date of Patent: Nov. 17, 2026

(54) DYNAMIC SYSTEM STATE CAPTURE FOR TROUBLESHOOTING OF MEDICAL DEVICES

(71) Applicant: GE Precision Healthcare LLC, Waukesha, WI (US)

(72) Inventors: Rama Krishna Reddy Narayana Reddy Gari, Brookfield, WI (US); Sridhar Madhavan, Barrington, IL (US); Mathews Matson Chavarukattil, Bengaluru (IN); Sai Kumar Muppalla, Bengaluru (IN)

(73) Assignee: GE Precision Healthcare LLC, Waukesha, WI (US)

( * ) Notice: Subject to any disclaimer, the term of this patent is extended or adjusted under 35 U.S.C. 154(b) by 223 days.

(21) Appl. No.: 18/776,758

(22) Filed: Jul. 18, 2024

(65) Prior Publication Data

US 2026/0024656 A1 Jan. 22, 2026

(51) Int. Cl.
*G16H 40/40* (2018.01)
*G16H 40/67* (2018.01)

(52) U.S. Cl.
CPC ............. *G16H 40/40* (2018.01); *G16H 40/67* (2018.01)

(58) Field of Classification Search
CPC ............................... G16H 40/40; G16H 40/67
USPC ......................................................... 705/2-3
See application file for complete search history.

(56) References Cited

U.S. PATENT DOCUMENTS 5,088,497 A 2/1992 Ikeda
5,528,168 A 6/1996 Kleveland
6,288,577 B1 9/2001 Wong
6,320,406 B1 11/2001 Morgan et al.
6,442,433 B1 * 8/2002 Linberg ............. A61N 1/37282 607/59

(Continued)

FOREIGN PATENT DOCUMENTS

CN 105342640 B 2/2016
CN 105913355 A 8/2016

(Continued)

OTHER PUBLICATIONS

Non-Final Office Action received for U.S. Appl. No. 18/426,572 dated May 5, 2025, 9 pages.

(Continued)

*Primary Examiner* — Michael Tomaszewski

(57) ABSTRACT

One or more systems, devices, computer program products and/or computer-implemented methods of use provided herein relate to dynamic system state capture for troubleshooting of medical devices. Accordingly, a system can comprise a memory that can store computer executable components. The system can further comprise a processor that can execute at least one of the computer executable components that can collect, in response to a service request in connection with a system failure of a medical device and via an artificial intelligence model, troubleshooting data based on a time range or an error type of the system failure. In various aspects, at least one of the computer executable components can further generate a system state digest of the troubleshooting data. In various instances, the system can further dynamically generate an encryption of the system state digest.

19 Claims, 23 Drawing Sheets

(56) References Cited

U.S. PATENT DOCUMENTS 6,650,149 B1 11/2003 Wong
6,691,134 B1 * 2/2004 Babula ..... A61B 6/00
7,949,444 B2 * 5/2011 Mukherjee ..... G10L 15/26 701/1
8,055,887 B2 * 11/2011 Karstens ..... G06K 1/00 713/1
8,407,158 B2 * 3/2013 Suri ..... H04L 41/5074 706/11
8,696,578 B2 4/2014 Kabakov et al.
8,738,663 B2 * 5/2014 Gonzalez ..... G06F 16/217 707/694
8,746,548 B2 * 6/2014 Terwilliger ..... G06F 16/9554 235/375
9,183,603 B2 * 11/2015 Borges ..... G16H 20/13
9,396,037 B2 * 7/2016 Morsi ..... G06F 9/5083
9,536,044 B2 * 1/2017 White ..... G16H 30/40
9,672,458 B2 * 6/2017 Burkhart ..... G06K 19/06037
9,734,448 B2 * 8/2017 Bolich ..... G06Q 10/20
10,025,791 B2 * 7/2018 Lee ..... G06Q 10/06
10,402,781 B2 * 9/2019 Terwilliger ..... G06Q 10/10
10,638,999 B2 * 5/2020 Shah ..... A61B 5/076
10,789,264 B2 * 9/2020 Crabtree ..... G06F 16/254
10,810,390 B2 * 10/2020 Hegendoerfer ..... G06K 7/10722
10,901,834 B2 * 1/2021 Abhinav ..... G06V 20/20
10,902,232 B2 * 1/2021 Peng ..... G06Q 20/3276
10,949,440 B2 * 3/2021 Schoueri ..... G06F 3/0643
11,087,878 B2 * 8/2021 Vesto ..... G16H 50/50
11,240,181 B1 * 2/2022 Nagaraja ..... G06N 3/006
11,309,060 B2 * 4/2022 Janevski ..... G16B 30/00
11,321,338 B2 * 5/2022 Okorafor ..... G06F 16/258
11,327,989 B2 * 5/2022 Wu ..... G06F 16/254
11,404,145 B2 * 8/2022 Saripalli ..... G06N 3/091
11,481,738 B2 * 10/2022 Tong ..... G06K 7/1417
11,599,729 B2 * 3/2023 Wu ..... G06F 16/3329
11,842,188 B2 * 12/2023 Bregman ..... G06F 11/3688
12,412,265 B2 * 9/2025 Doctor ..... G06T 7/0012
2004/0090265 A1 5/2004 Pradhan
2004/0093184 A1 * 5/2004 Hendrickson ..... G16H 40/40 702/184
2009/0043203 A1 2/2009 Pelissier et al.
2009/0125757 A1 * 5/2009 Knorl ..... G06F 11/30 714/47.1
2010/0168596 A1 7/2010 Jaeschke et al.
2010/0274145 A1 10/2010 Tupin, Jr. et al.
2010/0274750 A1 * 10/2010 Oltean ..... G06F 16/122 706/46
2011/0185035 A1 * 7/2011 Van ..... G06F 11/2294 715/764
2012/0053465 A1 3/2012 Kudoh
2012/0117425 A1 * 5/2012 Lam ..... G06Q 30/0251 714/E11.029
2013/0086573 A1 * 4/2013 Moritzen ..... G06F 8/65 717/171
2013/0087609 A1 * 4/2013 Nichol ..... G06F 16/9554 235/375
2013/0123637 A1 5/2013 Wohlschlager et al.
2013/0138452 A1 * 5/2013 Cork ..... G06Q 10/087 705/2
2013/0158407 A1 6/2013 Kabakov et al.
2013/0245436 A1 9/2013 Tupin, Jr. et al.
2014/0163378 A1 * 6/2014 Ohshima ..... A61B 8/145 600/447
2014/0276070 A1 9/2014 Kabakov et al.
2015/0146772 A1 * 5/2015 Fujimori ..... H04L 1/0002 375/238
2015/0302176 A1 * 10/2015 Lyons ..... G08B 21/24 705/2
2017/0071579 A1 * 3/2017 Ko ..... A61B 8/546
2018/0338746 A1 * 11/2018 Wu ..... A61B 8/54
2019/0019090 A1 * 1/2019 Chacko ..... G06Q 10/103
2019/0240414 A1 * 8/2019 Sjöstedt ..... G16H 40/40
2019/0244707 A1 * 8/2019 Becker ..... H04L 67/52
2019/0370035 A1 * 12/2019 Ramachandra Iyer ..... G06F 3/167
2019/0370671 A1 * 12/2019 Martinez Canedo ..... G06N 3/0475
2020/0013501 A1 * 1/2020 Page ..... G08B 21/24
2020/0210268 A1 * 7/2020 Nuthi ..... G05B 23/0275
2020/0210850 A1 * 7/2020 Nuthi ..... G06N 3/09
2020/0210966 A1 * 7/2020 Nuthi ..... G06N 20/00
2020/0211699 A1 * 7/2020 Nuthi ..... G16H 40/40
2020/0321108 A1 * 10/2020 Reid ..... G16H 40/67
2020/0337648 A1 * 10/2020 Saripalli ..... G16H 10/60
2020/0357513 A1 * 11/2020 Katra ..... A61N 1/37258
2020/0365262 A1 * 11/2020 Sreenivasan ..... G06F 11/30
2020/0380076 A1 * 12/2020 Taylor ..... G06F 40/289
2021/0004284 A1 * 1/2021 Vah ..... G06N 20/20
2021/0064932 A1 * 3/2021 Wang ..... G06F 16/3322
2021/0065888 A1 * 3/2021 Page ..... G06F 3/04847
2021/0241897 A1 * 8/2021 Casse ..... G16H 40/20
2021/0366601 A1 * 11/2021 Livoti ..... G16H 40/67
2021/0398054 A1 * 12/2021 Jaggers ..... G06Q 10/063112
2022/0005083 A1 * 1/2022 Patterson ..... G06F 16/90332
2022/0189618 A1 * 6/2022 Klassen ..... G16H 40/20
2022/0245799 A1 * 8/2022 Doctor ..... G05B 23/0216
2022/0293246 A1 * 9/2022 Tweedie ..... G16H 30/20
2022/0374300 A1 * 11/2022 Che ..... G06F 11/079
2023/0034748 A1 * 2/2023 Bull ..... G06F 3/1204
2023/0168895 A1 * 6/2023 Shah ..... G06F 11/3006 707/602
2023/0238103 A1 * 7/2023 Murphy ..... G16H 20/17 705/2
2023/0259821 A1 * 8/2023 Travalini ..... G06N 3/0455 706/12
2023/0260641 A1 * 8/2023 Tessmann ..... A61B 90/70 705/2
2023/0260642 A1 * 8/2023 Sullivan ..... G06Q 30/016 705/2
2023/0307118 A1 * 9/2023 Wang ..... G16H 40/40
2023/0334076 A1 * 10/2023 Hashish ..... G06F 16/338
2023/0335236 A1 * 10/2023 Dambman ..... G16H 10/40
2023/0335238 A1 * 10/2023 Danckwardt ..... A61B 5/0002
2023/0395246 A1 * 12/2023 Vogtmeier ..... A61B 6/586
2024/0038377 A1 * 2/2024 Ayers ..... G16H 40/40
2024/0055112 A1 * 2/2024 Uhlemann ..... G16H 40/40
2024/0094322 A1 * 3/2024 Bright ..... G01R 33/546
2024/0122555 A1 * 4/2024 Pawlak ..... A61B 6/03
2024/0161919 A1 * 5/2024 Kwan ..... G06Q 10/20
2024/0296352 A1 9/2024 Yanosy et al.
2024/0339206 A1 * 10/2024 Lee ..... G16H 40/20
2024/0404690 A1 * 12/2024 Demewez ..... G06Q 10/20
2025/0006355 A1 * 1/2025 Patil ..... G06F 40/20
2025/0078041 A1 * 3/2025 Shafie ..... G16H 40/40
2025/0149153 A1 * 5/2025 Matson Chavarukattil ..... G06F 40/205
2025/0258851 A1 * 8/2025 Lewis ..... G06N 20/00
2025/0299809 A1 * 9/2025 Weiß ..... G16H 40/40
2026/0024656 A1 * 1/2026 Narayana Reddy Gari ..... G16H 40/40
2026/0086538 A1 * 3/2026 Turlica ..... G05B 19/4184

FOREIGN PATENT DOCUMENTS

CN 108231145 A 6/2018
CN 110035303 A 7/2019
CN 111899852 A 11/2020
CN 112364148 A 2/2021
CN 114073546 A 2/2022
CN 114118062 A 3/2022
CN 114882979 A 8/2022
CN 114898848 A 8/2022
CN 115098673 A 9/2022
CN 115964460 A 4/2023
CN 114446423 B 6/2023
WO 2020/167316 A1 8/2020
WO 2022206822 A1 10/2022

(56) References Cited

FOREIGN PATENT DOCUMENTS

| | | | |
|---|---|---|---|
| WO | 2022/229088 | A1 | 11/2022 |
| WO | 2023/088983 | A1 | 5/2023 |

OTHER PUBLICATIONS

Deloitte, "Tech Trends 2021", Delotte Insights, https://www2.deloitte.com/content/dam/insights/articles/7023_TT-machine-data-revolution-feeding-the-machine/DI_2021-TT-machine-data-revolution.pdf, last accessed Nov. 2, 2023, 21 pages.

Anadiotis, George, "5 Technology Trends for the Roaring 20s, Part 2: AI, Knowledge Graphs, Infinity and Beyond", On-line publication on ZD NET, https://www.zdnet.com/article/5-technology-trends-for-the-roaring-20s-part-2-ai-knowledge-graphs-infinity-and-beyond/, Jan. 16, 2020, 9 pages.

Mcmahan et al., "Federated Learning: Collaborative Machine Learning without Centralized Training Data", Google Blog, https://ai.googleblog.com/2017/04/federated-learning-collaborative.html, Apr. 6, 2017, 5 pages.

Tensorflow, "TensorFlow Federated: Machine Learning on Decentralized Data", Online Available at URL: https://www.tensorflow.org/federated, last accessed Aug. 28, 2023, 4 pages.

Schema.org, Company website https://schema.org/, last accessed Aug. 28, 2023, 1 page.

Schema.org, "Iot and Schema.org: Getting Started", https://schema.org/docs/iot-gettingstarted.html, last accessed Sep. 19, 2023, 15 pages.

Maguire et al., "A Metadata-Based Architecture for User-Centered Data Accountability", Electron Markets, Online available at https://link.springer.com/article/10.1007/s12525-015-0184-z, vol. 25, 2015, pp. 155-160.

Non-Final office action received for U.S. Appl. No. 18/422,591 dated Dec. 20, 2024, 42 pages.

Chavarukattil, et al. "Generative Artificial Intelligence Driven Self-Healing Agent for Medical Devices" United States U.S. Appl. No. 18/749,679, filed Jun. 21, 2024, 37 pages.

* cited by examiner

300

302

System configuration details

```
<C>
<S  <system ID> />
<V <product version> />
<O <Host OS> />
<H <Console HW details> />
<I  <IP Address> />
<Z <time zone details> />
</C>
```

304

System resource details

```
<R> // Resource details
<M <memory details> />
<C <CPU details> />
<D <Disk details> />
<N <network details> />
</R>
```

306

System usage details

```
<U> // Usage details
 <SE <exam#> /> //Usage within an
exam
... // activity during exam
<EE/>
...
<SE <exam#> />  //Usage within an
exam
... // activity during exam
</EE/>

...

<R>  // Recon activity
...
</R>

<RF> //Reformat activity
...
</RF>

#  Service tools execution
<CSD entry/>
<CAL <cal name>/>
<CSD  exit>
...
</U>
```

308

System state/error details

```
<S <file/source>> // file/source name
<T<timestamp1>>E<error_code>;
<T<timestamp1>>E<error_code>;
<T<timestamp1>>E<error_code>;
...
</S>
....

<S <file/source>> //file/source name
<T<timestamp1>>E<error_code>;
<T<timestamp1>>E<error_code>;
<T<timestamp1>>E<error_code>;
...
</S>

....
```

FIG. 3

DYNAMIC SYSTEM STATE CAPTURE FOR TROUBLESHOOTING OF MEDICAL DEVICES

TECHNICAL FIELD

The subject disclosure relates generally to medical devices, and more specifically to dynamic system state capture for troubleshooting of medical devices.

BACKGROUND

A medical device can be deployed in the field. During deployment or operation of the medical device, the medical device can be offline and experience a system failure. A service request can be initiated by a user of the medical device with a support team to diagnose the system failure of the medical device. However, the user can provide inaccurate or inconsistent information about the system failure, limiting the support team to accurately diagnose the system failure. Existing techniques for collecting and transmitting troubleshooting data to the support team when the medical device is offline require manual collection and transferring of information. Unfortunately, such existing techniques are unhelpful.

Accordingly, systems or techniques that can address one or more of these technical problems can be desirable.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate dynamic system state capture for troubleshooting of medical devices are described.

According to one or more embodiments, a system is provided. The system can comprise a non-transitory computer-readable memory that can store computer-executable components. The system can further comprise a processor that executes at least one of the computer executable components that can collect, in response to a service request in connection with a system failure of a medical device and via an artificial intelligence model, troubleshooting data based on a time range or an error type of the system failure. In various aspects, the at least one of the computer executable components can further generate a system state digest of the troubleshooting data. In various instances, the at least one of the computer executable components can further dynamically generate an encryption of the system state digest.

According to one or more embodiments, a computer-implemented method is provided. In various embodiments, the computer-implemented method can comprise collecting, by a system operatively coupled to a processor and in response to a service request in connection with a system failure of a medical device, troubleshooting data based on a time range or an error type of the system failure via an artificial intelligence model. In various aspects, the computer-implemented method can comprise generating, by the system, a system state digest of the troubleshooting data. In various instances, the computer-implemented method can comprise dynamically generating, by the system, an encryption of the system state digest.

According to one or more embodiments, a computer program product for facilitating precision diagnostics and troubleshooting of medical devices is provided. In various embodiments, the computer program product can comprise a non-transitory computer-readable memory having program instructions embodied therewith. In various aspects, the program instructions can be executable by a processor to cause the processor to collect and in response to a service request in connection with a system failure of a medical device, troubleshooting data based on a time range or an error type of the system failure via an artificial intelligence model. In various cases, the program instructions can be further executable to cause the processor to generate a system state digest of the troubleshooting data. In various aspects, the program instructions can be further executable to cause the processor to dynamically generate an encryption of the system state digest.

DESCRIPTION OF THE DRAWINGS

FIG. 3 illustrates an example, non-limiting diagram of a format of the system state digest that can facilitate dynamic system state capture for troubleshooting of medical devices in accordance with one or more embodiments described herein.

DETAILED DESCRIPTION

Figure 1:
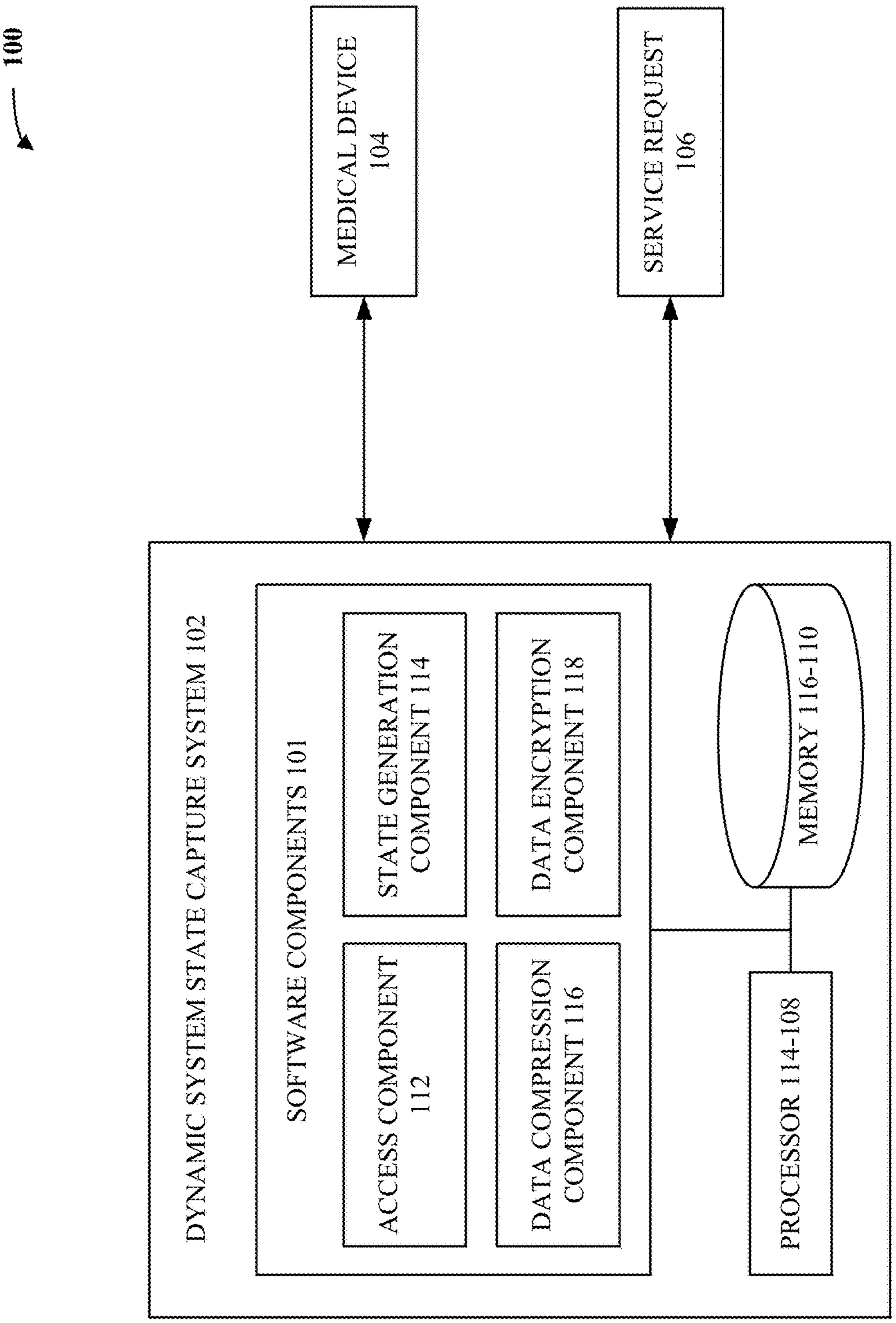
FIG. 1 illustrates a block diagram of an example, non-limiting system that facilitates dynamic system state capture for troubleshooting of medical devices in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A medical device (e.g., a computed tomography (CT) scanner, a magnetic resonance imaging (MRI) scanner, an X-ray scanner, an ultrasound scanner, a positron emission tomography (PET) scanner) can be deployed in the field. During deployment, the medical device can malfunction or experience a system failure. For instance, the medical device can experience a hardware failure or a software failure that impedes or prevents the medical device from properly functioning. As a non-limiting example, the medical device can experience a hardware disk failure. As another non-limiting example, the image reconstruction subsystem of the medical device (e.g., a medical image scanner) can fail to generate images. As yet another non-limiting example, the medical device's communication network can be suspended. In any case, it can be desirable to diagnose and remediate such system failures.

However, collecting troubleshooting data to diagnose the system failures and transmitting the troubleshooting data to a support team (e.g., back office, cloud backend) through a service request to determine a remediation for the system failures can prove challenging. So, the workflow to diagnose and remediate such system failures can be inefficient, time-consuming, and costly.

Existing techniques for collecting troubleshooting data require a user of the medical device to create a service request with the troubleshooting data or communicate the system failure verbally with a support team over a phone call. In particular, such existing techniques involve the user communicating what they believe describe symptoms exhibited by the medical device about the system failure. Unfortunately, such existing techniques are unhelpful. Indeed, the support team only receives information provided by the user, which can be prone to inaccuracies, inconsistencies, or otherwise does not accurately or properly describe symptoms of the malfunction or system failure. Thus, vital information for troubleshooting (e.g., error logs, detailed system configuration, error codes) is not communicated to the support team. Furthermore, the information needed to diagnose the system failure or malfunction can be voluminous. So, even if the user happens to accurately describe symptoms of the malfunction or system failure, verbally or manually communicating such information can be challenging and impractical (e.g., verbally communicating voluminous amounts of troubleshooting data over a phone call with the support team). For example, when the medical device is offline, the vital information needed for troubleshooting can be copied to media and transferred to the support team. However, transferring the information by physically shipping the media can be time-consuming. Alternatively, the information can be uploaded to a cloud backend and offloaded from the system. However, transferring the information through such an approach can be unreliable due to privacy and security restrictions on usage of the media.

Accordingly, systems or techniques that can address one or more of these technical problems can be desirable.

Various embodiments described herein can address one or more of these technical problems. One or more embodiments described herein can include systems, computer-implemented methods, apparatus, or computer program products that can facilitate dynamic system state capture for troubleshooting of medical devices. In particular, the inventors of various embodiments described herein realized that in an occurrence of a system failure of a medical device, collection of troubleshooting data can be inefficient and inaccurate. Indeed, the present inventors realized that users or operators of a medical device typically do not provide accurate or relevant information needed for resolving the system failure. Furthermore, transmitting the troubleshooting data to a cloud backend or back-office support team can require manual transmission of such data, especially if the medical device is offline. The inventors of various embodiments described herein realized that troubleshooting data can be efficiently collected and securely transmitted to the cloud backend or back-office support team by intelligently collected troubleshooting data and transmitting such data via scannable QR codes or encoded text. Accordingly, the qualified service technician can efficiently receive a remedial procedure plan to address or resolve the system failure after creation of a service request with little to no manual intervention (e.g., manual search or collection of troubleshooting data, manual transmission of troubleshooting data), even if the medical device is offline.

Accordingly, various embodiments described herein can be considered as improving how artificial intelligence can be leveraged to determine which troubleshooting data to collect and how the troubleshooting data can be securely transferred to solve malfunctions experienced by the medical device.

Various embodiments described herein can be considered as a computerized tool (e.g., any suitable combination of computer-executable hardware or computer-executable software) that can facilitate dynamic system state capture for troubleshooting of medical devices. In various aspects, such computerized tool can comprise an access component, a state generation component, a data compression component, or a data encryption component.

In various embodiments, there can be a medical device. In various aspects, the medical device can be any suitable type of medical equipment or modality (e.g., a CT scanner, an MRI scanner, an X-ray scanner, an ultrasound scanner, or a PET scanner, among others). In various instances, the medical device can be deployed in any suitable clinical or operational context (e.g., in a hospital, in a veterinary clinic, on an emergency vehicle). In various cases, the medical device can comprise any suitable human-computer interface device (e.g., keyboard, keypad, touchscreen, voice command system).

In various embodiments, the medical device can be associated with a service request. In various aspects, the service request can be any suitable electronic file that textually describes or otherwise indicates one or more hardware-based or software-based system failures that are exhibited or demonstrated by the medical device. In various instances, the service request can be electronically crafted, written, or generated by or at the behest of a user of the medical device (e.g., the user can do so via the human-computer interface device of the medical device). In various cases, the service request can be electronically crafted, written, or generated by an internal monitoring system or diagnostic software of the medical device upon detecting a malfunction.

In various embodiments, the access component of the computerized tool can electronically access the medical device or the service request. For instance, the access component can electronically communicate with (e.g., transmit data to, receive data from) the medical device. As another instance, the access component can electronically retrieve or obtain the service request from any suitable centralized or decentralized data structures (e.g., graph data structures, relational data structures, hybrid data structures), whether remote from or local to the access component. In any case, the access component can electronically access the medical device or the service request, such that other components of the computerized tool can electronically interact with (e.g., read, write, edit, copy, manipulate) the medical device or with the service request. In various aspects, the service request can comprise a time range of occurrence of the system failure. The service request can further comprise an error type of the system failure.

In various embodiments, the access component can electronically collect troubleshooting data (e.g., system configuration information, error logs, error codes) from the medical device in response to receiving the service request. The troubleshooting data can be considered as any data or information accessed from the medical device or service request, or any information or data electronically obtained from the user (e.g., via the human-computer interface device of the medical device). In various instances, the access component can determine, via an artificial intelligence model, which troubleshooting data to collect based on the time range or error type comprised in the service request.

In various embodiments, the state generation component of the computerized tool can electronically generate a system state digest of the troubleshooting data collected from the medical device via the access component. The system state digest is a compressed (e.g., summarized) representation of the state of the medical device's system when the system failure occurred.

In various embodiments, the data compression component of the computerized tool can electronically interact with (e.g., read, write, edit, copy, manipulate) the system state digest. For instance, the data compression component can analyze the system state digest generated by the state generation component. In various instances, the data compression component can reduce the data size of the system state digest (e.g., by exploiting redundancies within the data, compressing the data into a structured format), by applying statistical methods).

In various embodiments, the data encryption component of the computerized tool can electronically interact with (e.g., read, write, edit, copy, manipulate) the system state digest. For instance, the data encryption component can encrypt the system state digest or a compression of the system state digest (e.g., compressed by data compression component). In various instances, the data encryption component can facilitate such encryption by digitally signing the system state digest using a cryptographic key.

Various embodiments described herein can be employed to use hardware or software to solve problems that are highly technical in nature (e.g., to facilitate dynamic system state capture for troubleshooting of medical devices), that are not abstract and that cannot be performed as a set of mental acts by a human. Further, some of the processes performed can be performed by a specialized computer (e.g., graphical user interfaces, data encryption, deep learning neural networks) for carrying out defined acts related to medical devices. For example, such defined acts can include: collecting, by a device operatively coupled to a processor and in response to a service request in connection with a system failure of a medical device, troubleshooting data based on a time range or an error type of the system failure via an artificial intelligence model; generating, by the device, a system state digest of the troubleshooting data; and dynamically generating, by the device, an encryption of the system state digest. Moreover, in various embodiments, such defined acts can include: generating one or more QR codes that encapsulates the system state digest in response to the medical device being offline; or generating encoded text of the system state digest in response to the medical device being online. Furthermore, in various instances, such defined acts can include: training, by the device, an artificial intelligence model on the service request and on knowledge graphs, wherein the service request is treated as a training input for the deep learning neural network, and wherein the knowledge graph is treated as a ground-truth annotation corresponding to the service request.

Such defined acts are not performed manually by humans. Indeed, neither the human mind nor a human with pen and paper can electronically compress or encrypt troubleshooting data of a system failure of a medical device (e.g., CT scanner, X-ray scanner), electronically generate QR codes or encoded text of encrypted data (e.g., encrypted system state digest), and electronically train an artificial intelligence model on knowledge graphs. Indeed, medical devices, graphical user interfaces, and artificial intelligence models are inherently-computerized, hardware-and-software-based constructs that simply cannot be meaningfully implemented or trained in any way by the human mind without computers. A computerized tool that can electronically train an artificial intelligence model to collect relevant troubleshooting data based on a system failure of a medical device is likewise inherently-computerized and cannot be implemented in any sensible, practical, or reasonable way without computers.

Moreover, various embodiments described herein can integrate into a practical application various teachings relating to dynamic system state capture for troubleshooting of medical devices. As described above, when a medical device experiences a malfunction, existing techniques involve a user or owner of that medical device manually determining, collecting, and communicating troubleshooting data to a support team or cloud backend. Such data collection and transmission is time-consuming and often inaccurate (e.g., the user or owner is prone to providing insufficient, incorrect, or inconsistent information).

Various embodiments described herein can address one or more of these technical problems. In particular, the present inventors recognized that users or operators of medical devices typically don't know which information is relevant to a system failure of a medical device or how to collect such information. Instead, as the present inventors realized, troubleshooting data can be intelligently collected so as to collect only relevant data to reduce size of the troubleshooting data to transmit. As described herein, various embodiments can involve collecting troubleshooting data that is relevant to remediating the system failure via an artificial intelligence model. In various aspects, such relevant troubleshooting data can be used to generate a system state digest that can subsequently be compressed and encoded into one or more QR codes or encoded text for secure transmitting of data to a cloud backend or back-office support team. Accordingly, once received by the cloud backend or back-office support team, the encrypted system state digest can be decrypted and decompressed to obtain the system state digest containing the relevant troubleshooting data. As described herein, various embodiments can further involve generating a remedial procedure plan by the cloud backend based on the obtained relevant troubleshooting data. Accordingly, the remedial procedure plan can be transmitted back to the user or operator. In this way, the user or owner of the medical device need not manually search, collect, or transmit troubleshooting data when the medical device is offline. Instead, the user or owner can efficiently receive a remedial procedure plan after creation of a service request to resolve the system failure. For at least these reasons, various embodiments described herein be considered as an improved technique for automatically identifying and securely transmitting relevant troubleshooting information for a system failure of a medical device. Thus, various embodiments described herein certainly constitute a tangible and concrete technical improvement or technical advantage in the field of medical devices (e.g., existing techniques are not able to automatically and effectively identify which data about a medical device is relevant for troubleshooting the medical device in the occurrence of a system failure). Accordingly, such embodiments clearly qualify as useful and practical applications of computers.

Furthermore, various embodiments described herein can control real-world tangible devices based on the disclosed teachings. For example, various embodiments described herein can electronically control real-world graphical user interfaces and can electronically train or execute real-world artificial intelligence models.

It should be appreciated that the herein figures and description provide non-limiting examples of various embodiments and are not necessarily drawn to scale.

FIG. 1 illustrates a block diagram of an example, non-limiting system 100 that can facilitate dynamic system state capture for troubleshooting of medical devices in accordance with one or more embodiments described herein. As shown, a dynamic system state capture system 102 can be electronically integrated, via any suitable wired or wireless electronic connections, with a medical device 104 or with a service request 106.

In various embodiments, the medical device 104 can be any suitable device, equipment, or modality. As a non-limiting example, the medical device 104 can be a CT scanner that can capture or generate CT scanned pixel arrays or voxel arrays. As another non-limiting example, the medical device 104 can be an MRI scanner that can capture or generate MRI scanned pixel arrays or voxel arrays. As even another non-limiting example, the medical device 104 can be an X-ray scanner that can capture or generate X-ray scanned pixel arrays or voxel arrays. As yet another non-limiting example, the medical device 104 can be an ultrasound scanner that can capture or generate ultrasound scanned pixel arrays or voxel arrays. As still another non-limiting example, the medical device 104 can be a PET scanner that can capture or generate PET scanned pixel arrays or voxel arrays.

In various aspects, the medical device 104 can be deployed, stationed, or otherwise implemented in any suitable clinical operational context. As a non-limiting example, the medical device 104 can be deployed, stationed, or otherwise implemented within any suitable hospital or medical center. As another non-limiting example, the medical device 104 can be deployed, stationed, or otherwise implemented within any suitable scientific or medical laboratory. As yet another non-limiting example, the medical device 104 can be deployed, stationed, or otherwise implemented within any suitable veterinary center. As even another non-limiting example, the medical device 104 can be deployed, stationed, or otherwise implemented within or onboard any suitable vehicle (e.g., ambulance, cruise ship, airplane).

In various instances, the medical device 104 can comprise any suitable human-computer interface device by which a user or operator of the medical device 104 can manually interact with or control the medical device 104. As a non-limiting example, the medical device 104 can comprise any suitable keyboard or keypad that can be pressed by the user or operator. As another non-limiting example, the medical device 104 can comprise any suitable computer mouse that can be dragged or clicked by the user or operator. As even another non-limiting example, the medical device 104 can comprise any suitable touchscreen that can be tactilely manipulated by the user or operator. As yet another non-limiting example, the medical device 104 can comprise any suitable voice command system that can accept verbal instructions spoken by the user or operator.

In various cases, the service request 106 can be any suitable electronic data (e.g., one or more scalars, one or more vectors, one or more matrices, one or more tensors, one or more character strings, or any suitable combination thereof) that indicates, specifies, or otherwise conveys one or more malfunction symptoms that the medical device 104 is afflicted with or is otherwise experiencing. As a non-limiting example, the service request 106 can be a plain text or structured text electronic file that describes such one or more malfunction symptoms. In various aspects, the user or operator of the medical device 104 can generate or otherwise cause the service request 106 to be created, by interacting with the human-computer interface device of the medical device 104 (e.g., by typing the service request 106 into a keyboard or touchscreen of the medical device 104, by speaking the service request 106 into a voice command system of the medical device 104). However, this is a mere non-limiting example. In other cases, the user or operator of the medical device 104 can generate or otherwise cause the service request 106 to be created, by interacting with any other suitable computing device. As another non-limiting example, the service request 106 can be created by an internal monitoring system or diagnostic software of the medical device 104 upon detecting a system failure. In various cases, the service request 106 can be written in any suitable language, such as English, French, or Spanish.

In various embodiments, the dynamic system state capture system 102 can comprise a processor 108 (e.g., computer processing unit, microprocessor) and a non-transitory computer-readable memory 110 that is operably or operatively or communicatively connected or coupled to the processor 108. The non-transitory computer-readable memory 110 can store computer-executable instructions which, upon execution by the processor 108, can cause the processor 108 or other components of the dynamic system state capture system 102 (e.g., component 101, access component 112, state generation component 114, data compression component 116, data encryption component 118) to perform one or more acts. In various embodiments, the non-transitory computer-readable memory 110 can store computer-executable components (e.g., ac component 101, access component 112, state generation component 114, data compression component 116, data encryption component 118), and the processor 108 can execute the computer-executable components.

In various embodiments, the dynamic system state capture system 102 can comprise an access component 112. In various aspects, the access component 112 can electronically access the medical device 104 or the service request 106. As a non-limiting example, the access component 112 can electronically communicate in any suitable fashion with the medical device 104. That is, the access component 112 can electronically transmit any suitable electronic data to the medical device 104, and the medical device 104 can likewise electronically transmit any suitable electronic data to the access component 112. As another non-limiting example, the access component 112 can electronically retrieve or otherwise electronically obtain the service request 106 from any suitable centralized or decentralized data structures (not shown) or from any suitable centralized or decentralized computing devices (not shown). Indeed, in some cases, the access component 112 can electronically receive the service request 106 from the medical device 104. In any case, the access component 112 can electronically access the medical device 104 or the service request 106, such that other components of the dynamic system state capture system 102 can electronically interact with the medical device 104 or with the service request 106.

In various embodiments, the access component 112 can electronically collect troubleshooting data (e.g., system configuration information, error logs, error codes) from the medical device 104 in response to receiving the service request. The troubleshooting data can be considered as any data or information accessed from the medical device 104 or service request, or any information or data electronically obtained from the user (e.g., via the human-computer interface device of the medical device 104). In various instances, the access component 112 can determine which troubleshooting data to collect based on a time range or an error type of a system failure comprised in the service request. Various non-limiting aspects are described with respect to FIG. 2.

In various embodiments, there can be any suitable number of distinct service requests (e.g., multiple instances of 106) corresponding to the medical device 104 (e.g., corresponding to any instantiation of the medical device 104, where distinct instantiations can be deployed in distinct operational contexts). Accordingly, the access component 112 can collect, as described above, respective troubleshooting data for each of those distinct service requests.

In various embodiments, the dynamic system state capture system 102 can comprise state generation component 114 can electronically generate a system state digest (e.g., system state digest 210) of the troubleshooting data collected from the medical device 104 via the access component 112.

In various embodiments, the dynamic system state capture system 102 can comprise data compression component 116 can electronically interact with the system state digest. For instance, the data compression component 116 can analyze the system state digest generated by the state generation component 114. In various instances, the data compression component 116 can reduce the data size of the system state digest (e.g., exploiting redundancies within the data, removing repeated sequences of characters, applying statistical methods).

In various embodiments, the dynamic system state capture system 102 can comprise data encryption component 118 can electronically interact with the system state digest. For instance, the data encryption component 118 can encrypt the system state digest or a compression of the system state digest (e.g., compressed by data compression component 116). In various instances, the data encryption component 118 can facilitate such encryption by digitally signing the system state digest using a cryptographic key. Various non-limiting aspects of encrypting the system state digest are described with respect to FIG. 15.

Figure 2:
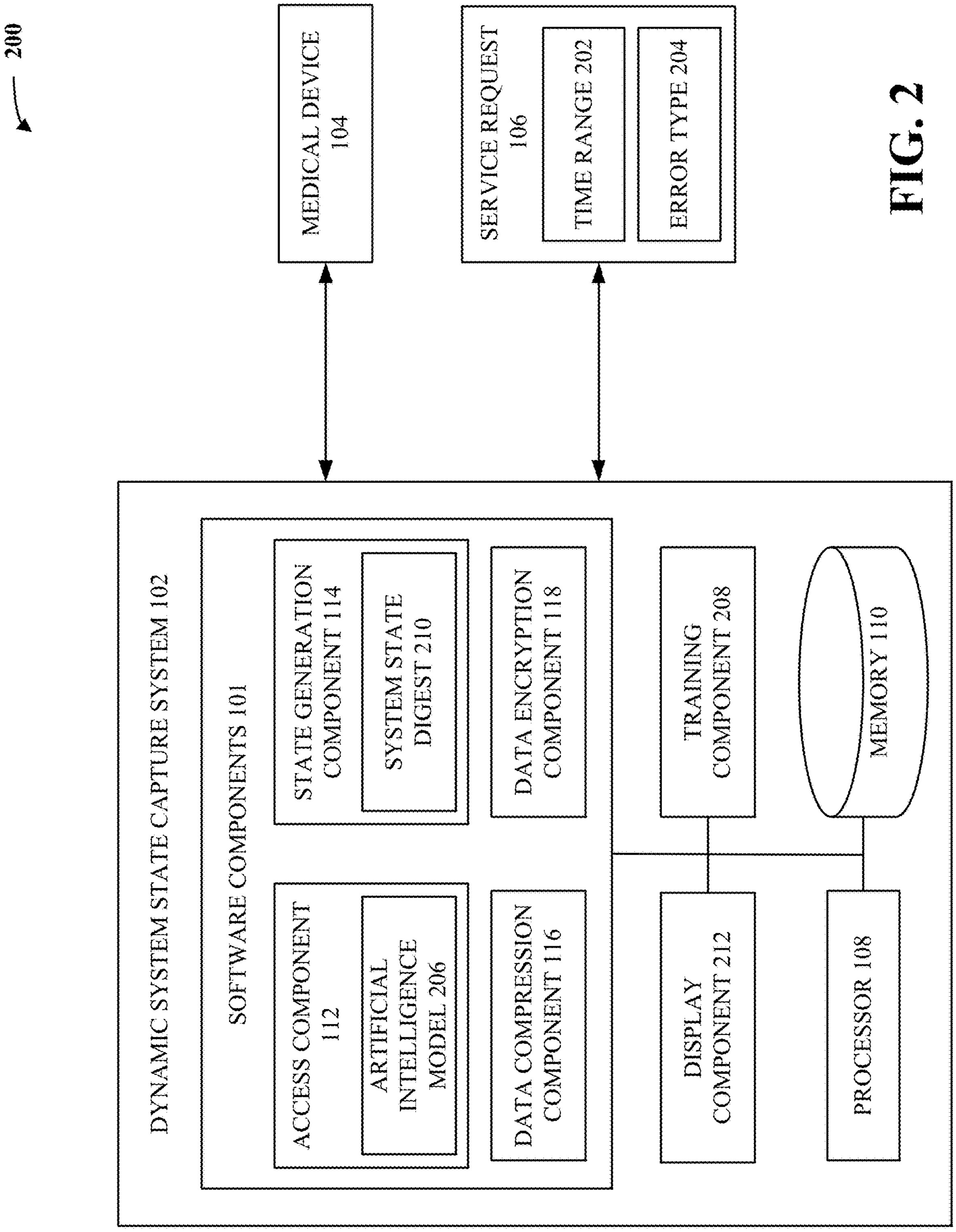
FIG. 2 illustrates a block diagram of an example, non-limiting system that facilitates dynamic system state capture for troubleshooting of medical devices in accordance with one or more embodiments described herein.

FIG. 2 illustrates a block diagram of an example, non-limiting system 200 that facilitates dynamic system state capture for troubleshooting of medical devices in accordance with one or more embodiments described herein. As shown, the system 200 can, in some cases, comprise the same components as the system 100, and can further comprise an artificial intelligence model 206, a training component 208, a system digest 210, and a display component 212.

In various embodiments, the service request 106 can comprise a time range 202 and an error type 204. The time range 202 can be any suitable electronic data (e.g., one or more scalars, one or more vectors, one or more matrices, one or more tensors, one or more character strings, or any suitable combination thereof). In various aspects, the time range 202 can identify a duration of time before and after the occurrence of the system failure. More specifically, the time range 202 can indicate an interval of time before the occurrence of an error indicator exhibited by medical device 104 and an interval of time after the occurrence of the error indicator.

In various instances, the error type 204 can be any suitable electronic data (e.g., one or more scalars, one or more vectors, one or more matrices, one or more tensors, one or more character strings, or any suitable combination thereof). For instance, the error type 204 can be natural language text entered by the user or operator on a graphical user interface comprised by display component 212. In other instances, the error type 204 can be converted into natural text from audio data recorded from the user or operator (e.g., by speaking the error type 204 into a voice command system of the medical device 104). As non-limiting examples, the error type 204 can be any suitable natural language text that can describe the system failure (e.g., sentences, a phrase), such as "The medical device is failing to generate images." or "will not generate scans". In other instances, the error type 204 can be selected by the user or operator from a pre-defined list of system failures (e.g., the user or operator selects between "hardware failure", "software failure", or "other").

In various embodiments, the state generation component 114 can generate system state digest 210 of troubleshooting data collected by access component 112. In various aspects, the system state digest 210 can comprise default data and custom data. The default data can comprise troubleshooting data that is collected via access component 112 irrespective of the error type 204 of the system failure of the medical device 104. As non-limiting examples, the default data can comprise system configuration data (e.g., HW/SW specification, software licenses, apps installed, software updates applied, time zone, OS, IP or MAC addresses, network ports, gateway information, proxy settings, security patches), system resource metrics (e.g., GPU, network, disk, IO, CPU), or system usage information (e.g., start or end of exams, recon or reformats, launch of service desktop or tools, key user actions). The custom data can comprise troubleshooting data that is collected based on the error type 204 of the system failure of the medical device 104 (e.g., error indicators, error codes, related sensor data, event data). In particular, which troubleshooting data to collect can be determined via artificial intelligence model 206. For instance, if the error type 204 is a scan abort, the artificial intelligence model 206 can determine to collect error codes or sensor data that occurred from a scan subsystem of the medical device 104. In various aspects, the service technician can, during such troubleshooting, interact with the graphical user interface of the display component 212.

In various aspects, the display component 212 can comprise or otherwise be electronically integrated with any suitable graphical user interface (e.g., graphical user interface 404). In various aspects, the graphical user interface can comprise any suitable electronic display (e.g., computer screen, computer monitor) and any suitable human-computer interface device (e.g., keyboard, keypad, touchscreen).

In various embodiments, the artificial intelligence model 206 can comprise a deep learning neural network. In various instances, the training component 208 can electronically train the deep learning neural network on the service request 106 and on knowledge graphs (e.g., knowledge graph 800). More specifically, the training component 208 can electronically store, maintain, control, or otherwise access the deep learning neural network. In various aspects, the deep learning neural network can exhibit any suitable internal architecture. For example, the deep learning neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the deep learning neural network can include any suitable numbers of neurons in various layers (e.g., different layers can have the same or different numbers of neurons as each other). As yet another example, the deep learning neural network can include any suitable activation functions (e.g., softmax, sigmoid, hyperbolic tangent, rectified linear unit) in various neurons (e.g., different neurons can have the same or different activation functions as each other). As still another example, the deep learning neural network can include any suitable interneuron connections or interlayer connections (e.g., forward connections, skip connections, recurrent connections).

In various cases, if the deep learning neural network has not yet undergone any training, the training component 208 can randomly initialize the trainable internal parameters (e.g., convolutional kernels, weight matrices, bias vectors) of the deep learning neural network. In contrast, if the deep learning neural network has already undergone at least some training, the training component 208 can refrain from re-initializing the trainable internal parameters of the deep learning neural network.

In various aspects, the training component 208 can execute the deep learning neural network on the service request 106, thereby causing the deep learning neural network to produce some output. In particular, the training component 208 can feed the service request 106 to an input layer of the deep learning neural network, the service request 106 can complete a forward pass through one or more hidden layers of the deep learning neural network, and such forward pass can cause an output layer of the deep learning neural network to compute the output based on activations provided by the one or more hidden layers.

Note that the format, size, or dimensionality of the output can be controlled or otherwise dictated by the number, arrangement, or sizes of the neurons or of other internal parameters (e.g., convolutional kernels) that are contained in or that otherwise make up the output layer of the deep learning neural network. So, the output can be forced to have any suitable or any desired format, size, or dimensionality, by adding, removing, or otherwise adjusting neurons or other internal parameters to, from, or within the output layer of the deep learning neural network. So, the output can be considered as predicted or inferred troubleshooting data to collect that the deep learning neural network believes should correspond to the service request 106 (e.g., believes is relevant to resolve or address the service request 106). In various cases, if the deep learning neural network has so far undergone no or little training, the output can be highly inaccurate (e.g., can be very different from the knowledge graphs).

In any case, the training component 208 can compute an error or loss (e.g., mean absolute error (MAE), mean squared error (MSE), cross-entropy error) between the output and the knowledge graph. In various aspects, the training component 208 can update the trainable internal parameters of the deep learning neural network by performing backpropagation (e.g., stochastic gradient descent) driven by the computed error or loss.

In various aspects, such training procedure can be repeated for any suitable number of service-request-and-knowledge-graph pairs. Such training can ultimately cause the trainable internal parameters of the deep learning neural network to become iteratively optimized for accurately inferring knowledge graph mappings based on inputted service requests. Note that the training component 208 can implement any suitable training batch sizes, any suitable training termination criteria, or any suitable error, loss, or objective functions.

In various instances, after such training, the training component 208 can electronically deploy the deep learning neural network as a third-party service. As a non-limiting example, a third-party who owns or operates an instantiation of the medical device can provide or create a given service request, and the training component 208 can execute the deep learning neural network on that given service request. Such execution can cause the deep learning neural network to produce predicted knowledge graph mappings, where such predicted knowledge graph mappings can be considered as indicating troubleshooting data (in the opinion of the deep learning neural network) that is relevant to solve or address the given service request. Accordingly, the third-party need not manually collect, search, or send troubleshooting data. Instead, the deep learning neural network can be leveraged to infer or predict which troubleshooting data to collect so as to efficiently troubleshoot the given service request.

In any case, the troubleshooting data, as described hereon, can be considered as the troubleshooting data determined relevant to collect by the artificial intelligence model 206 (e.g., the deep learning neural network) based on service request 106. In various instances, the troubleshooting data that is collected can exhibit any suitable size or length. Nevertheless, the state generation component 114 can generate the system state digest 210 of the troubleshooting data (e.g., troubleshooting data relevant to solve or address service request 106). Accordingly, the data compression component 116 can compress the system state digest 210 and the data encryption component 118 can encrypt the system state digest 210. In various embodiments, the encryption component 118 can generate one or more QR codes or encoded text of the system state digest 210 depending on the size of the system state digest 210.

FIG. 3 illustrates an example, non-limiting diagram 300 of a format of the system state digest that can facilitate dynamic system state capture for troubleshooting of medical devices in accordance with one or more embodiments described herein.

In various embodiments, the state generation component 114 can generate a concise format of the troubleshooting data as the system state digest 210. For instance, the system state digest 210 can comprise a structured format (e.g., XML) containing tags to identify or label the troubleshooting data. As a non-limiting example, the system state digest 210 can comprise system configuration details in concise format 302, system resource details in concise format 304, system usage details in concise format 306, and system error details in concise format 308. As shown, the concise formats contained in system state digest 210 can comprise various tags to identify the data (e.g., root tags, sub-element tags, closing tags). For example, the system configuration details in concise format 302 can be identified by root tag <C>, closing tag </C>, and comprise sub-elements such as <V> that store the product version of the software running on the system of the medical device 104. As another example, system error details in concise format 308 can be identified by root tag <S> which identifies a source file, closing tag </S>, and comprise sub-elements such as <T> that store timestamps of an error codes that occurred in the system of the medical device 104. However, these are mere non-limiting examples. In other cases, the system state digest 210 can comprise any suitable concise or structured format of the troubleshooting data.

Figure 4:
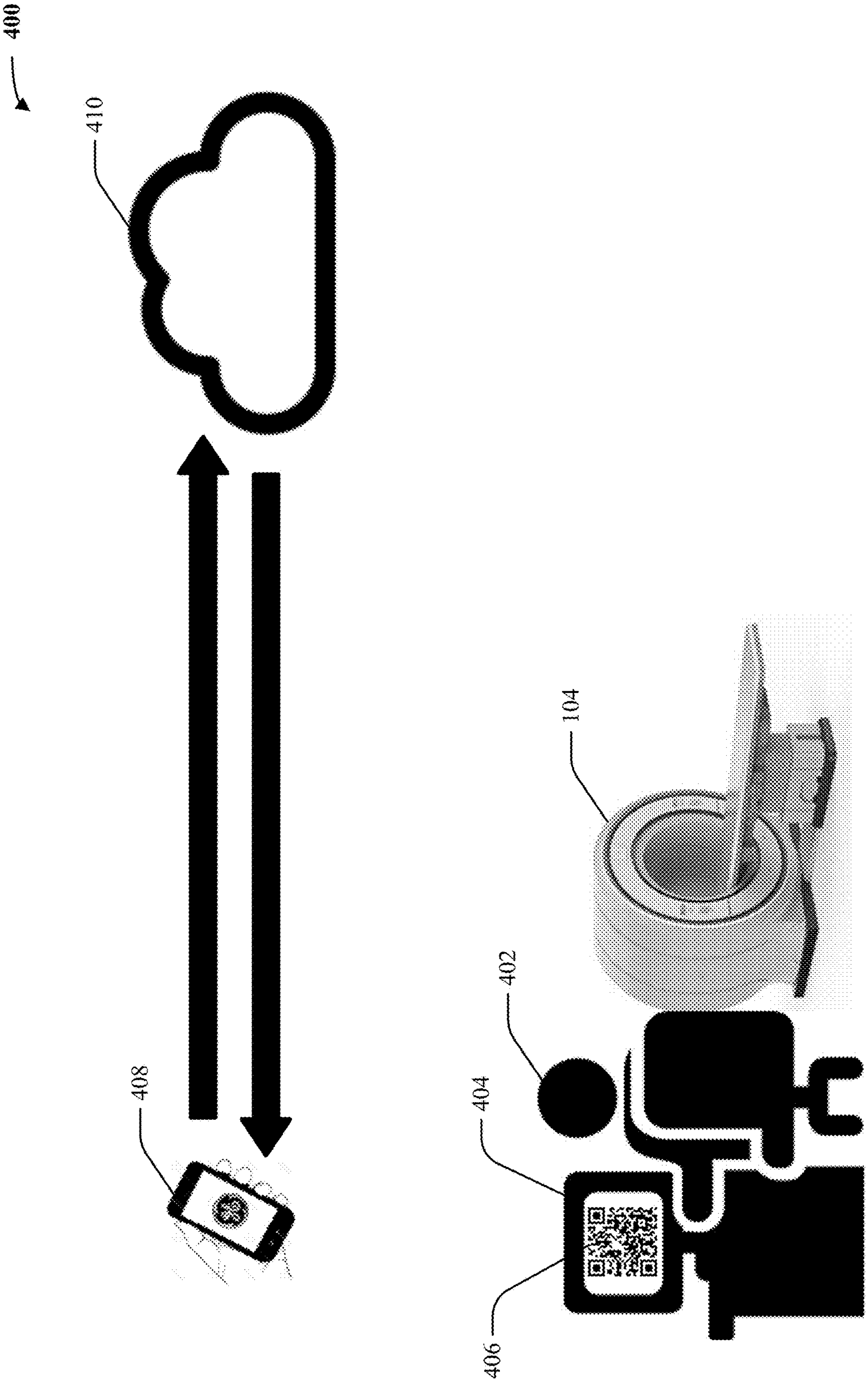
FIG. 4 illustrates an example, non-limiting diagram of dynamic system state capture for troubleshooting of offline medical devices in accordance with one or more embodiments described herein.

FIG. 4 illustrates an example, non-limiting diagram 400 of dynamic system state capture for troubleshooting of offline medical devices in accordance with one or more embodiments described herein.

Diagram 300 depicts a non-limiting example use case of troubleshooting medical device 104 when medical device 104 is offline. In such instances, the system of the medical device 104 can not directly or automatically transmit troubleshooting data to a cloud backend 410 (e.g., back office, support team) when it is offline. Therefore, service request 106 must be initiated or created in response to experiencing a system failure of medical device 104 (e.g., created by user 402 or automatically created by internal monitoring system of medical device 104). In various aspects, in response to creation of service request 106, wherein service request 106 comprises time range 202 and error type 204 of the system failure, the access component 112 can initiate data collection of the troubleshooting data. Following collection of troubleshooting data via artificial intelligence model 206, the state generation component 112 can generate system state digest 210 of the troubleshooting data. Accordingly, the data compression component 116 can compress system state digest 210 and the data encryption component 118 can generate an encryption of system state digest 210. In various embodiments, the data encryption component 118 generate one or more QR codes 406 of the encryption of system state digest 210. In instances where the size of the system state digest 210 is too large to encapsulate into one or more QR codes 406, the data encryption component 118 generate encoded text (e.g., encoded text 902).

In various embodiments, the data encryption component 118 can engage the display component 212 to electronically control or otherwise electronically access a graphical user interface 404. In various aspects, the graphical user interface 404 can comprise any suitable electronic display, such as a computer screen or a computer monitor. In various instances, the graphical user interface 404 can further comprise any suitable human-computer interface device, such as a keyboard, keypad, or voice command system. In some cases, the electronic display of the graphical user interface 404 can be an interactive touchscreen. In various aspects, the display component 116 can visually render the one or more QR codes 406 (e.g., or the encoded text depending on the size of system state digest 210) on the graphical user interface 404, such that the user 402 can view the one or more QR codes 406 by viewing or interacting with the graphical user interface 404.

In various aspects, the encryption of system state digest 210 can be transmitted to cloud backend 410 in response to scanning of the QR codes 406. In various embodiments, the user 402 can scan the QR codes 406 via a mobile device 408. In various aspects, the mobile device 408 can be any suitable device capable of electronically scanning via photos or video. The QR codes 406 can be scanned using any number of scans (e.g., one photo, more than one photo, a video, a photo and a video). In any case, the cloud backend 410 can receive the encryption of system state digest 210 that is encapsulated in the QR codes 406, even if the medical device 104 is offline. In response to the cloud backend 410 receiving the encryption of system state digest 210, the encryption of system state digest 210 can be decrypted and decompressed to obtain the system state digest 210. Non-limiting aspects of decryption and decompression are discussed with respect to FIGS. 12, 13, and 15.

In various embodiments, there can be a second artificial intelligence model (e.g., artificial intelligence model 1304) of the cloud backend 410. In various aspects, the second artificial intelligence model can generate a remedial procedure plan based on the system state digest 210. The remedial procedure plan can contain content relevant to remediating the system failure of the medical device 104 (e.g., content that the second artificial intelligence model believes is relevant to solve or address the system failure). The remedial procedure plan can comprise any suitable format, size, or dimensionality. For instance, the remedial procedure plan can contain video content, text data, augmented reality (AR) content, virtual reality (VR) content, images, or any suitable combination thereof.

In various instances, the cloud backend 410 can send the remedial procedure plan back to the mobile device 408, wherein the user 402 can view the remedial procedure plan on the mobile device. Accordingly, the user 402 can follow the remedial procedure plan to resolve the system failure of the medical device 104.

Figure 5:
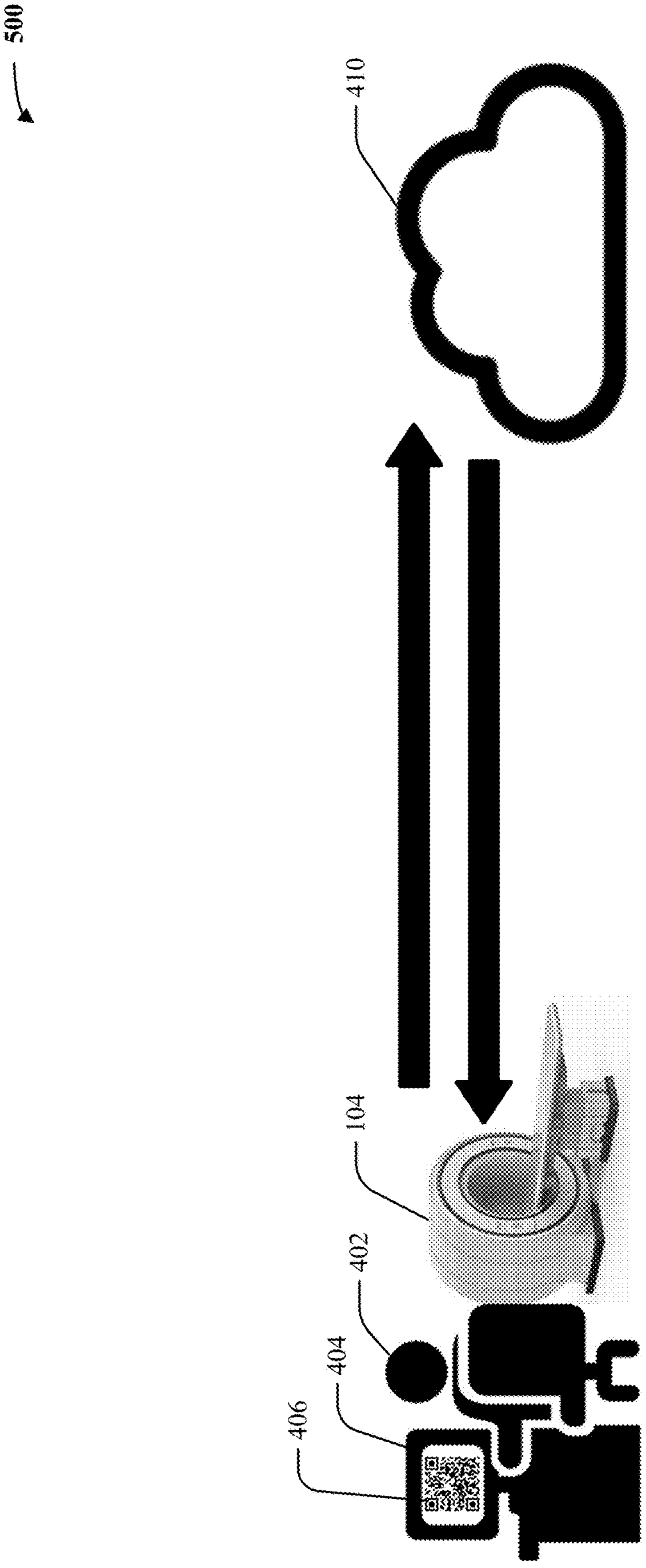
FIG. 5 illustrates an example, non-limiting diagram of dynamic system state capture for troubleshooting of online medical devices in accordance with one or more embodiments described here.

FIG. 5 illustrates an example, non-limiting diagram 500 of dynamic system state capture for troubleshooting of online medical devices in accordance with one or more embodiments described here.

The various embodiments described herein can be employed to resolve system failures of online medical devices as well as offline medical devices. Diagram 300 depicts a non-limiting example use case of troubleshooting medical device 104 when medical device 104 is online. In various instances, service request 106 can be initiated or created in response to experiencing a system failure of medical device 104 (e.g., created by user 402 or automatically created by internal monitoring system of medical device 104). In various aspects, in response to creation of service request 106, wherein service request 106 comprises time range 202 and error type 204 of the system failure, the access component 112 can initiate data collection of the troubleshooting data. Following collection of troubleshooting data via artificial intelligence model 206, the state generation component 112 can generate system state digest 210 of the troubleshooting data. Accordingly, the data compression component 116 can compress system state digest 210 and the data encryption component 118 can generate an encryption of system state digest 210. In various embodiments, the data encryption component 118 can generate an encryption of system state digest 210 (e.g., as encoded text).

In various embodiments, the data encryption component 118 can engage the display component 212 to electronically control or otherwise electronically access the graphical user interface 404. In various aspects, the display component 116 can visually render the encoded text or encryption of the system state digest 210 on the graphical user interface 404. In various instances, the display component 116 can refrain from visually rendering the encoded text or encryption of the system state digest 210 on the graphical user interface 404. In either case, the encryption of system state digest 210 can be automatically transmitted to cloud backend 410. That is, the encryption of the system state digest 210 can be sent to the cloud backend 410 without scanning of the encoded text or the encryption by user 402 via a mobile device.

In response to the cloud backend 410 receiving the encryption of system state digest 210, the encryption of system state digest 210 can be decrypted and decompressed to obtain the system state digest 210.

In various embodiments, the second artificial intelligence model can generate a remedial procedure plan based on the system state digest 210. The remedial procedure plan can contain content relevant to remediating the system failure of the medical device 104 (e.g., content that the second artificial intelligence model believes is relevant to solve or address the system failure). The remedial procedure plan can comprise any suitable format, size, or dimensionality. For instance, the remedial procedure can contain video content, text data, augmented reality (AR) content, virtual reality (VR) content, or images.

In various instances, the cloud backend 410 can send the remedial procedure plan back to the medical device 104, wherein the user 402 can view the remedial procedure plan on the graphical user interface 404. That is, the display component 212 can visually render the remedial procedure plan on graphical user interface 404 of the medical device 104. In some cases, the cloud backend 410 can also send the remedial procedure plan to mobile device 408 of user 402. Accordingly, the user 402 can follow the remedial procedure plan to resolve the system failure of the medical device 104. In various aspects, some steps to resolve the system failure can be automatically executed in medical device 104 if the medical device 104 is equipped with suitable hardware and/or software to facilitate such automatic execution.

Figure 6:
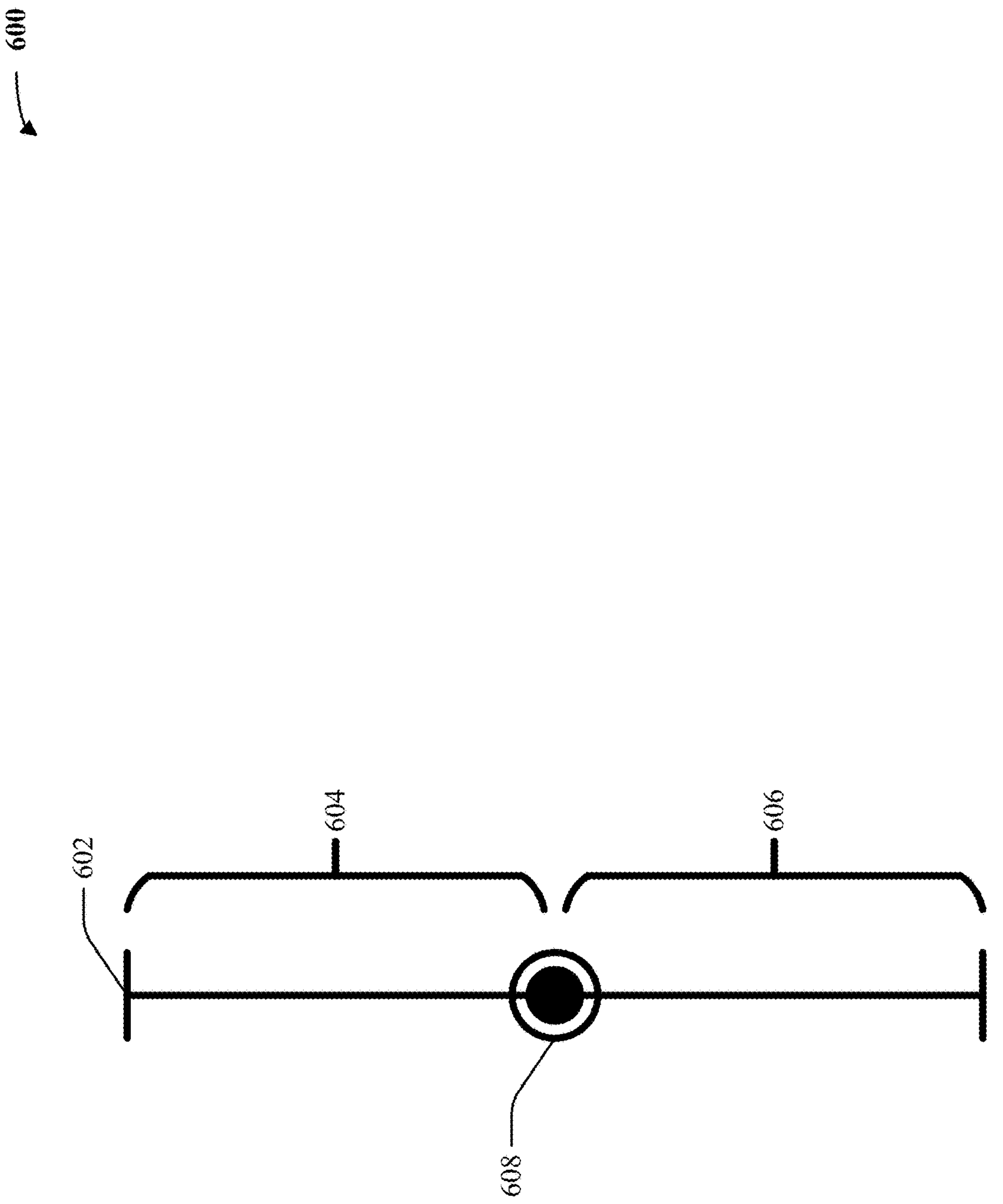
FIG. 6 illustrates an example, non-limiting diagram of a time range of a system failure of a medical device in accordance with one or more embodiments described herein.

FIG. 6 illustrates an example, non-limiting diagram 600 of a time range of a system failure of a medical device in accordance with one or more embodiments described herein.

In various embodiments, the service request 106 can comprise time range 202. Diagram 500 shows, as an example, the time range 202 describing a system failure of medical device 104. Within a time interval 602, a key error indicator of a system failure (e.g., error indicator relevant or pertaining to the system failure) can occur at epicenter 608 with interval 604 occurring before the key error indicator and interval 606 occurring after the key error indicator.

In various instances, endpoints of the interval 602 can be identified by user 402 or operator of the medical device 104. In other cases, the endpoints of the interval 602 can be automatically identified by an internal monitoring system or diagnostic software of the medical device 104 upon detecting a system failure. In any case, it can be desirable to collect troubleshooting data from the time range 202 to limit or minimize the volume of troubleshooting data by only collecting necessary data for diagnosing the system failure. For instance, in the occurrence of a system failure, error logs can be collected as troubleshooting data. However, such error logs can be noisy, meaning they contain a plurality of other error indicators that do not pertain or relate to the system failure of interest. Thus, limiting the error logs to be collected by time range 202 and identifying epicenter 608 of the key error indicator can reduce the volume of troubleshooting data to collect and enable efficient data collection and diagnosis of the system failure. That is, the volume of troubleshooting data sent to the cloud backend 212 can be limited by occurrence within time interval 602.

Figure 7:
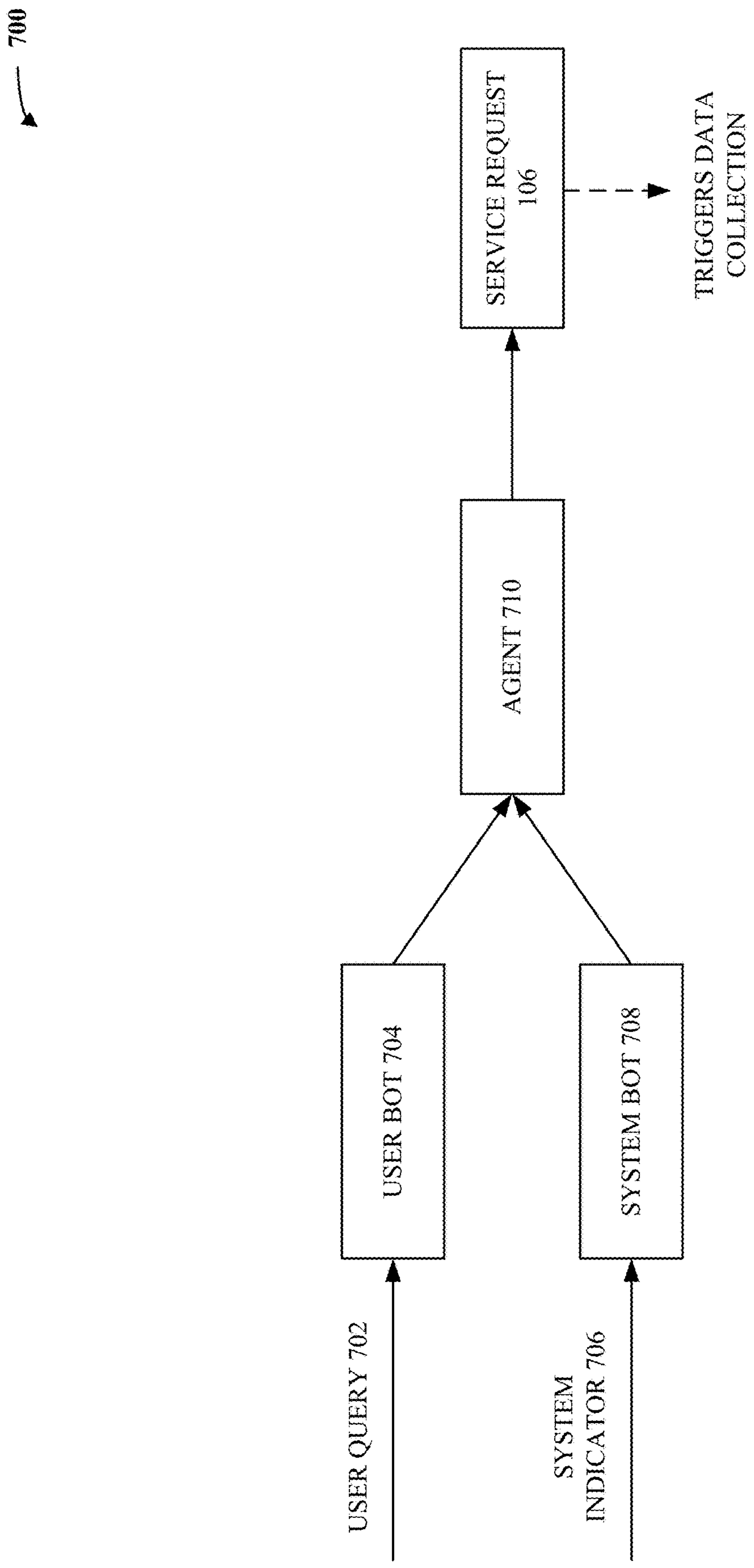
FIG. 7 illustrates a block diagram of an example, non-limiting process of generating a service request for facilitating dynamic system state capture for troubleshooting of medical devices in accordance with one or more embodiments described herein.

FIG. 7 illustrates a block diagram of an example, non-limiting process 700 of generating a service request for facilitating dynamic system state capture for troubleshooting of medical devices in accordance with one or more embodiments described herein.

In various embodiments, the service request 106 can be initiated by user 402 or any operator of medical device 104 or by an internal monitoring system or diagnostic software of the medical device 104 upon detecting a system failure. The user 402 can initiate creation of service request 106 via any suitable software. For instance, on any suitable electronic display of graphical user interface 404, the user 402 can interact with a user bot 704. That is, the user bot 704 can receive a user query 702 (e.g., user-initiated service request 106) from user 402. As a non-limiting example, the user bot 704 can be an intelligent service assistant chatbot where the user 402 can, on the graphical user interface 404, select an application for initiating service request 106. The application can comprise any suitable interface that can receive, on graphical user interface 404, details of the system failure from user 402. Specifically, the user 402 can input time range 202 and error type 204. That is, the user bot 704 can prompt the user 402 to enter time range 202 of the system failure. For instance, the user 402 can enter an estimated time range in which the system failure occurred (e.g., an estimated start time and an estimated end time). In other instances, the user 402 can enter an exact time of occurrence (e.g., if known by user 402) of the system failure as time range 202.

Furthermore, the user bot 704 can prompt the user 402 to enter error type 204 of the system failure. In various aspects, the error type 204 can be natural language text entered by user 402 (e.g., natural language text that describes the system failure). In other instances, the error type 204 can be selected by user 402 from a pre-defined list of error types. In yet other instances, the user bot 704 can receive error type 204 through voice (e.g., if medical device 104 is equipped with a voice command system). That is, user 402 can input error type 302 to user bot 704 by vocally describing the system failure. In any case, the error type 204 can describe the system failure in any suitable fashion (e.g., described in sentences, describe by a phrase, a selected error type description).

Note that, this is a non-limiting example, and the medical device 104 can be equipped with any suitable software and/or applications that can enable user 402 to initiate creation of service request 106 and input details about the system failure (e.g., time range 202, error type 204).

In various embodiments, the service request 106 can be automatically initiated. For system-initiated service requests, a system bot 708 can receive a system indicator 706. The system indicator 706 can comprise any suitable format, size, or dimensionality. For instance, the system indicator 706 can be an error code that is identified by an internal monitoring system or diagnostic software of the medical device 104. In various aspects, the system bot 708 can determine time range 202 and error type 204 based on the system indicator 706 and without input from user 402. In some cases, the user 402 can be prompted, on the electronic display, to confirm and/or edit the time range 202 and error type 204 that was determined by system bot 708. That is, the graphical user interface 404 can visually render, depict, or otherwise illustrate the time range 202 and error type 204 that was determined by system bot 708, and receive a confirmation or updated time range 202 and error type 204 of the system failure.

No matter how the service request 106 is initiated (e.g., user-initiated or system-initiated), an agent 710 can receive time range 202 and error type 204. In some embodiments, the agent 710 can analyze or interpret time range 202 and error type 204. For instance, agent 710 can be a tool-augmented large language model (TALM). A tool-augmented large language model is a type of AI that combines the capabilities of a standard large language model (LLM) with specialized tools. In various embodiments, the access component 112 can electronically store, electronically maintain, electronically control, or otherwise electronically access the agent 710. In various embodiments, the agent 710 can employ the TALM to analyze the natural language text of the time range 202 and error type 204 to identify the key error indicators of the system failure and occurrences of the key error indicators. In response the identifying the key error indicators of the system failure and occurrences of the key error indicators, the agent 710 can create service request 106 and trigger data collection of the troubleshooting data.

Figure 8:
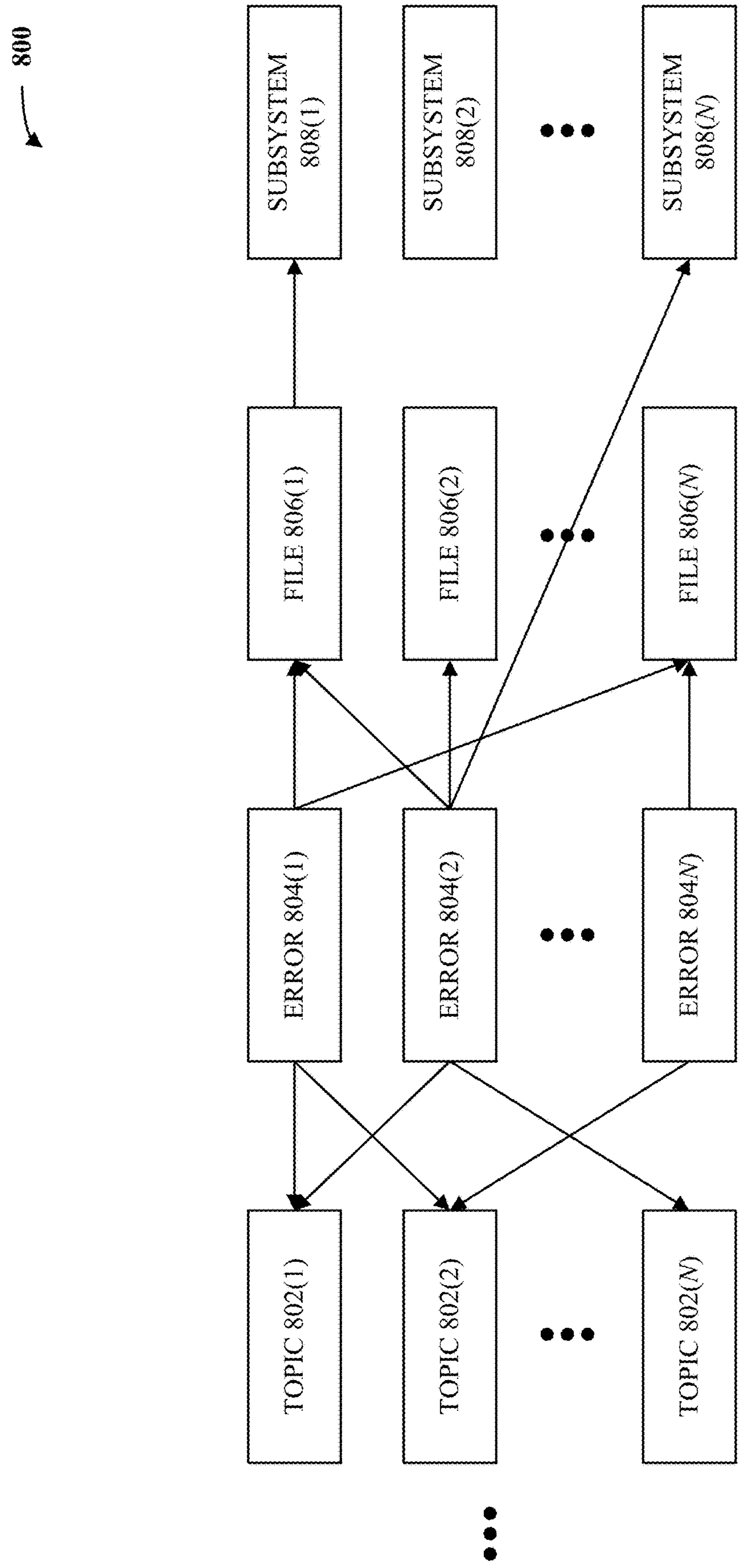
FIG. 8 illustrates a diagram of an example, non-limiting knowledge graph for facilitating dynamic system state capture for troubleshooting of medical devices in accordance with one or more embodiments described herein.

FIG. 8 illustrates a diagram of an example, non-limiting knowledge graph 800 for facilitating dynamic system state capture for troubleshooting of medical devices in accordance with one or more embodiments described herein.

In various aspects, the non-limiting knowledge graph 800 can represent or otherwise convey the relationships between various attributes or entities relevant to system failures or troubleshooting data. Specifically, for instance, the non-limiting knowledge graph 800 can represent or otherwise convey the relationships between errors 804, topics 802 (e.g., types of data), files 806 (e.g., file locations of troubleshooting data), subsystems 808 (e.g., components), and/or other attributes. That is, the non-limiting knowledge graph 800 can comprise mappings between errors 804 and one or more attributes (e.g., topics 802, files 806, subsystems 808). The mappings in non-limiting knowledge graph 800 are connections that link entities and/or attributes, defining how the entities and/or attributes in the mapping are related. The mappings of non-limiting knowledge graph 800 can be defined by the set of relations present within non-limiting knowledge graph 800.

In various instances, the non-limiting knowledge graph 800 can comprise nodes (e.g., the various attributes or entities) and relations between nodes. Accordingly, the nodes can be interrelated to each other via a plurality of relations. Non-limiting examples of such relations can include: a subject-of relation; a part-of relation; a hyponym-of relation; a nested-within relation; a contains relation; a symptom-of relation; a caused-by relation; or a condition-precedent relation. Note that, in various cases, the relations can be considered as being knowledge graph edges that are coupled to the nodes of the knowledge graph.

For instance, the non-limiting knowledge graph 800 can comprise nodes representing topics 802. There can be k topics for any suitable positive integer k: a topic 802(1) to a topic 802(*k*). Similarly, the non-limiting knowledge graph 800 can comprise nodes representing errors 804. There can be l errors 804 for any suitable positive integer l: an error 804(1) to an error 804(*l*). Moreover, as shown, the non-limiting knowledge graph 800 can comprise nodes representing files 806. There can be m files 806 for any suitable positive integer m: a file 806(1) to a file 806(*m*). Even further, the non-limiting knowledge graph 800 can comprise nodes representing subsystems 806. There can be n subsystems 808 for any suitable positive integer n: a subsystem 808(1) to a subsystem 808(*n*). As shown, the non-limiting knowledge graph 800 can comprise relations between the topics 802, errors 804, files 806, subsystems, and/or other attributes.

For example, there can be a relation between error 804(1) (e.g., "disk failure") and file 806(*n*) (e.g., "system_logs.txt")

documented in. This can indicate that the file "system_logs.txt" contains information about the "disk failure" error, such as error codes or troubleshooting steps. As another example, there can be a relation between error 804 (2) (e.g., "network timeout") and topic 802(1) (e.g., "user login data") associated with. This can indicate that the "network timeout" error is likely to occur when dealing with "user login data," suggesting a potential correlation between the two. As yet another example, there can be a relation between file 806(1) (e.g., a firmware update file "bios_update.exe") and a subsystem (e.g., "motherboard") updates. This can indicate that the "bios_update.exe" file is designed to update the firmware of the "motherboard" subsystem for troubleshooting compatibility issues. As even another example, there can be a relation between error 804 (2) (e.g., "Display flickering") and subsystem 808(*n*) (e.g., "graphics card") associated with. This can indicate that the "Display flickering" error is often linked to problems within the "graphics card" subsystem, guiding collection of troubleshooting data towards that component.

Note that, this is a non-limiting example of a knowledge graph that can facilitate dynamic system state capture for troubleshooting of medical devices, and the knowledge graph can comprise any suitable attributes, entities, and relations between such attributes and/or entities. In any case, the non-limiting knowledge graph 800 can be used to train artificial intelligence model 206. That is, the artificial intelligence model 206 can be trained using any suitable knowledge graph and on any number of knowledge graphs.

Figure 9:
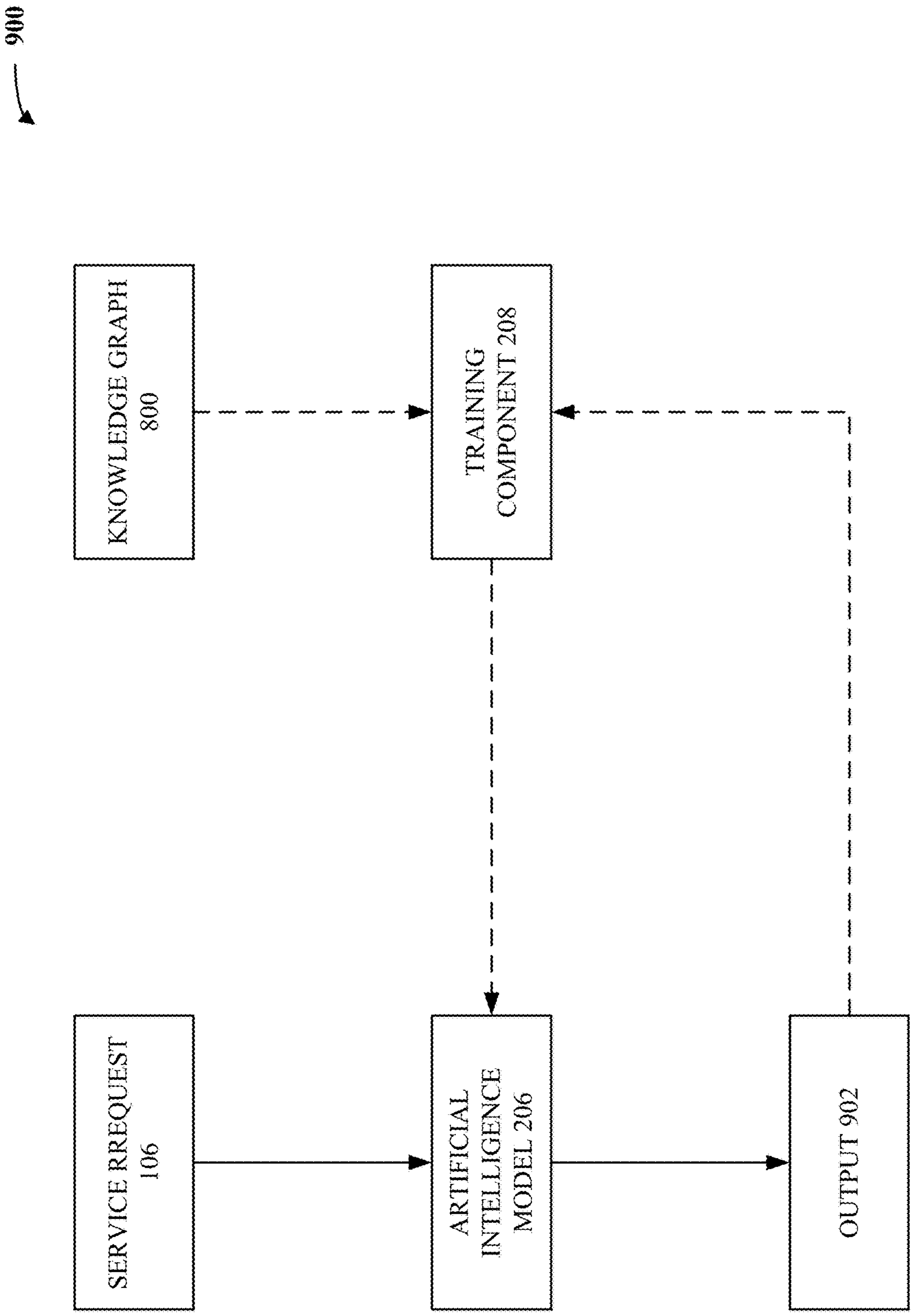
FIG. 9 illustrates a block diagram of an example, non-limiting process of training an artificial intelligence model for facilitating dynamic system state capture for troubleshooting of medical devices in accordance with one or more embodiments described herein.

FIG. 9 illustrates a block diagram of an example, non-limiting process 900 of training an artificial intelligence model for facilitating dynamic system state capture for troubleshooting of medical devices in accordance with one or more embodiments described herein.

Prior to beginning such training, the training component 208 can initialize in any suitable fashion (e.g., random initialization) the trainable internal parameters (e.g., weight matrices, bias vectors, convolutional kernels) of the artificial intelligence model 206 (e.g., the deep learning neural network).

In various aspects, the training component 208 can electronically execute the artificial intelligence model 206 on the service request 106, and such execution can cause the artificial intelligence model 206 to produce an output 902. More specifically, as mentioned above, the service request 106 can be one or more scalars, one or more vectors, one or more matrices, one or more tensors, or one or more character strings. Accordingly, the training component 208 can feed the service request 106 (e.g., can feed whatever scalars, vectors, matrices, tensors, or character strings that define the service request 106) to an input layer of the artificial intelligence model 206. In various instances, the service request 106 (e.g., whatever scalars, vectors, matrices, tensors, or character strings that define the service request 106) can complete a forward pass through one or more hidden layers of the artificial intelligence model 206. In various cases, an output layer of the artificial intelligence model 206 can compute the output 902, based on activation maps yielded by the one or more hidden layers.

Note that the format, size, or dimensionality of the output 902 can be dictated by the number, arrangement, sizes, or other characteristics of the neurons, convolutional kernels, or other internal parameters of the output layer (or of any other layers) of the artificial intelligence model 206. Accordingly, the output 902 can be forced to have a format, size, or dimensionality that is the same as, comparable to, or otherwise commensurate with that of the knowledge graph 800. Thus, the output 902 can be considered as a predicted or inferred knowledge graph that the artificial intelligence model 206 believes should correspond to the service request 106. In other words, the output 902 can be considered as a predicted or inferred relations between errors 804 and various attributes or entities indicating relevant troubleshooting data that the artificial intelligence model 206 believes would solve or address the service request 106. In contrast, the knowledge graph 800 can be considered as the ground-truth knowledge graph that is known or deemed to correspond to the service request 106. That is, the knowledge graph 800 can be the correct or accurate set of relations between errors 804 and various attributes or entities indicating relevant troubleshooting data that is known or deemed to solve or address the service request 106. Note that, if the artificial intelligence model 206 has so far undergone no or little training, then the output 902 can be highly inaccurate (e.g., can be very different from the knowledge graph 800).

In various aspects, the training component 208 can compute any suitable error or loss (e.g., MAE, MSE, cross-entropy) between the output 902 and the knowledge graph 800. In various instances, the training component 208 can update the trainable internal parameters of the artificial intelligence model 206, by performing backpropagation (e.g., stochastic gradient descent) driven by the computed error or loss.

In various aspects, the above-described training procedure can be repeated for any suitable number of service-request-knowledge-graph tuples (e.g., for each service-request-knowledge-graph tuple acquired by the access component 112). Such training can ultimately cause the trainable internal parameters of the artificial intelligence model 206 to become iteratively optimized for accurately or correctly inferring knowledge graphs (e.g., for accurately or correctly inferring relations between errors 804 and various attributes or entities indicating relevant troubleshooting data) in response to inputted service requests. In various cases, the training component 208 can implement any suitable training termination criterion, any suitable training batch sizes, or any suitable error, loss, or objective functions when training the artificial intelligence model 206.

In any case, the artificial intelligence model 206 can thus be trained or configured to receive as input any service request associated with an instantiation of the medical device 104, and to determine as output which troubleshooting data should be collected so as to solve or address that service request.

Figure 10:
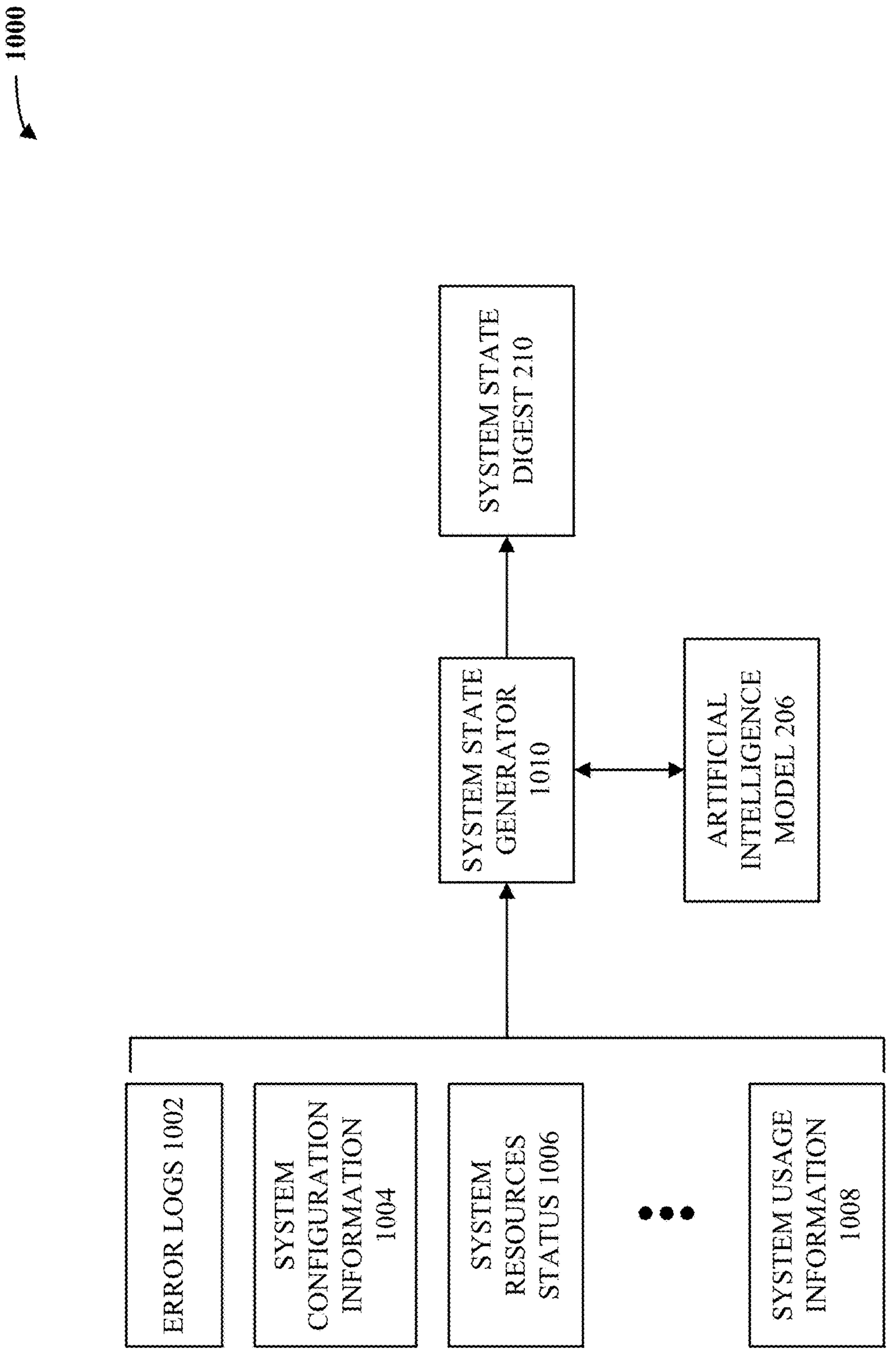
FIG. 10 illustrates a block diagram of an example, non-limiting process of generating a system state digest for facilitating dynamic system state capture for troubleshooting of medical devices in accordance with one or more embodiments described herein.

FIG. 10 illustrates a block diagram of an example, non-limiting process 1000 generating a system state digest for facilitating dynamic system state capture for troubleshooting of medical devices in accordance with one or more embodiments described herein.

In various embodiments, the access component 112 can collect the troubleshooting data. For instance, the troubleshooting data can comprise error logs 1002, system configuration information 1004, system resources status 1006, system usage information 1008, and/or any other suitable troubleshooting data. That is, the troubleshooting data can be any data collected within time range 202. In various aspects, error logs 1002 can comprise any suitable record of error events that occurred within medical device 104 (e.g., error types, error times). In various instances, the system configuration information 1004 can be any suitable data that describes a current setup or settings of medical device 104 (e.g., hardware configuration, software versions, network settings). Further, in various cases, the system resources status 1006 can comprise any suitable information that describes the current state or availability of system resources of medical device 104 (e.g., CPU usage, memory usage, disk space, network bandwidth). In various aspects, the system usage information 1008 can comprise any suitable data that describes how the system is being used (e.g., user activities, application usage patterns, workload statistics).

In various aspects, the troubleshooting data can be input into system state generator 1010. The system state generator 1010 can comprise or electronically access artificial intelligence model 1010. The access component 112 can electronically store, maintain, control, or otherwise access the system state generator 1010. In response to system state generator 1010 receiving the troubleshooting data, the artificial intelligence model 1010 can determine which troubleshooting data is relevant to the system failure of the medical device 104 (e.g., troubleshooting data that is known or deemed to solve or address the service request 106 in the opinion of the artificial intelligence model 206). Accordingly, the access component 112 can collect such relevant troubleshooting data to generate system state digest 210.

Figure 11:
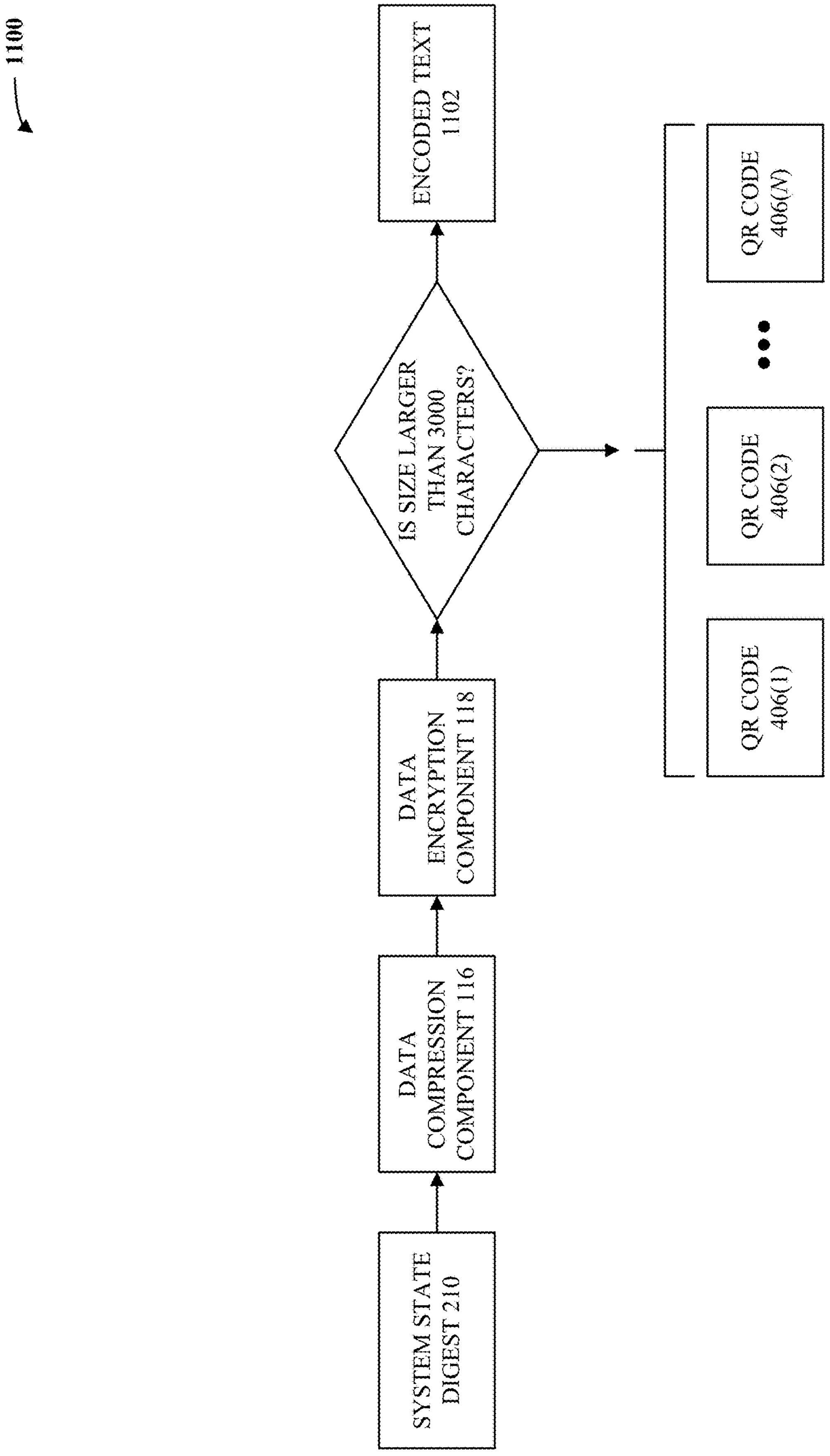
FIG. 11 illustrates a block diagram of an example, non-limiting process generating quick response (also referred to herein as "QR") codes or encoded text for facilitating dynamic system state capture for troubleshooting of medical devices in accordance with one or more embodiments described herein.

FIG. 11 illustrates a block diagram of an example, non-limiting process 1100 generating QR codes or encoded text for facilitating dynamic system state capture for troubleshooting of medical devices in accordance with one or more embodiments described herein.

In various embodiments, the system state digest 210 can be compressed (e.g., via data compression component 116) and encrypted (e.g., via data encryption component 118). In various aspects, the data encryption component 118 can then generate one or more QR codes 406 or encoded text 1102. Generating the one or more QR codes 406 or encoded text 1102 cam comprise determining if the size of the system state digest 210 (after compression and encryption) is larger than a defined character limit. For instance, the generating the one or more QR codes 406 or encoded text 1102 cam comprise determining if the size of the system state digest 210 is larger than or at least 3000 characters, although the defined character limit can be defined as any suitable size. If the size of the system state digest 210 is smaller than (e.g., or at most) 3000 characters (e.g., or the defined character limit), the data encryption component 118 can then generate one or more QR codes 406. Conversely, if the size of the system state digest 210 is larger than (e.g., or at least) 3000 characters (e.g., or the defined character limit), the data encryption component 118 can then generate encoded text 1102. The one or more QR codes 406 can comprise N QR codes for any positive integer N: a QR code 406(1) to a QR code 406(N).

Figure 12:
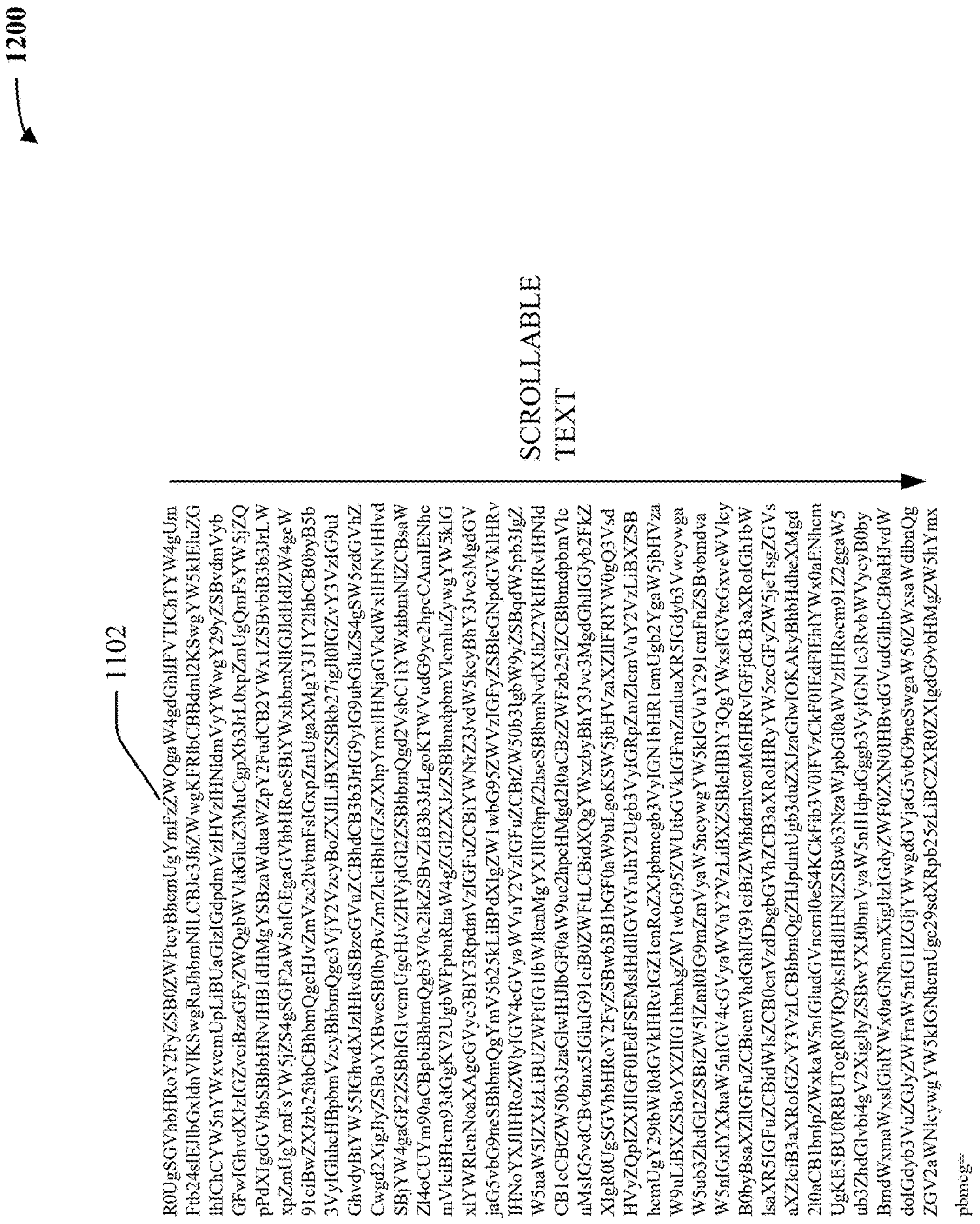
FIG. 12 illustrates a diagram an example, non-limiting encoded text for facilitating dynamic system state capture for troubleshooting of medical devices in accordance with one or more embodiments described herein.

FIG. 12 illustrates a diagram an example, non-limiting encoded text 1100 for facilitating dynamic system state capture for troubleshooting of medical devices in accordance with one or more embodiments described herein.

Depicted in FIG. 12 is a non-limiting example of encoded text 1102 that can be generated by encryption component 118 based on system state digest 210. The encoded text 1102 can be displayed on graphical user interface 404 of the electronic display of medical device 104. In some instances, user 402 can interact with graphical user interface 404 to scroll through the encoded text 1102, so as to view and/or scan the entirety of encoded text 1102. In other words, the graphical user interface 404 can visually render, depict, or otherwise illustrate the encoded text 1102 as scrollable text on the electronic display.

Figure 13:
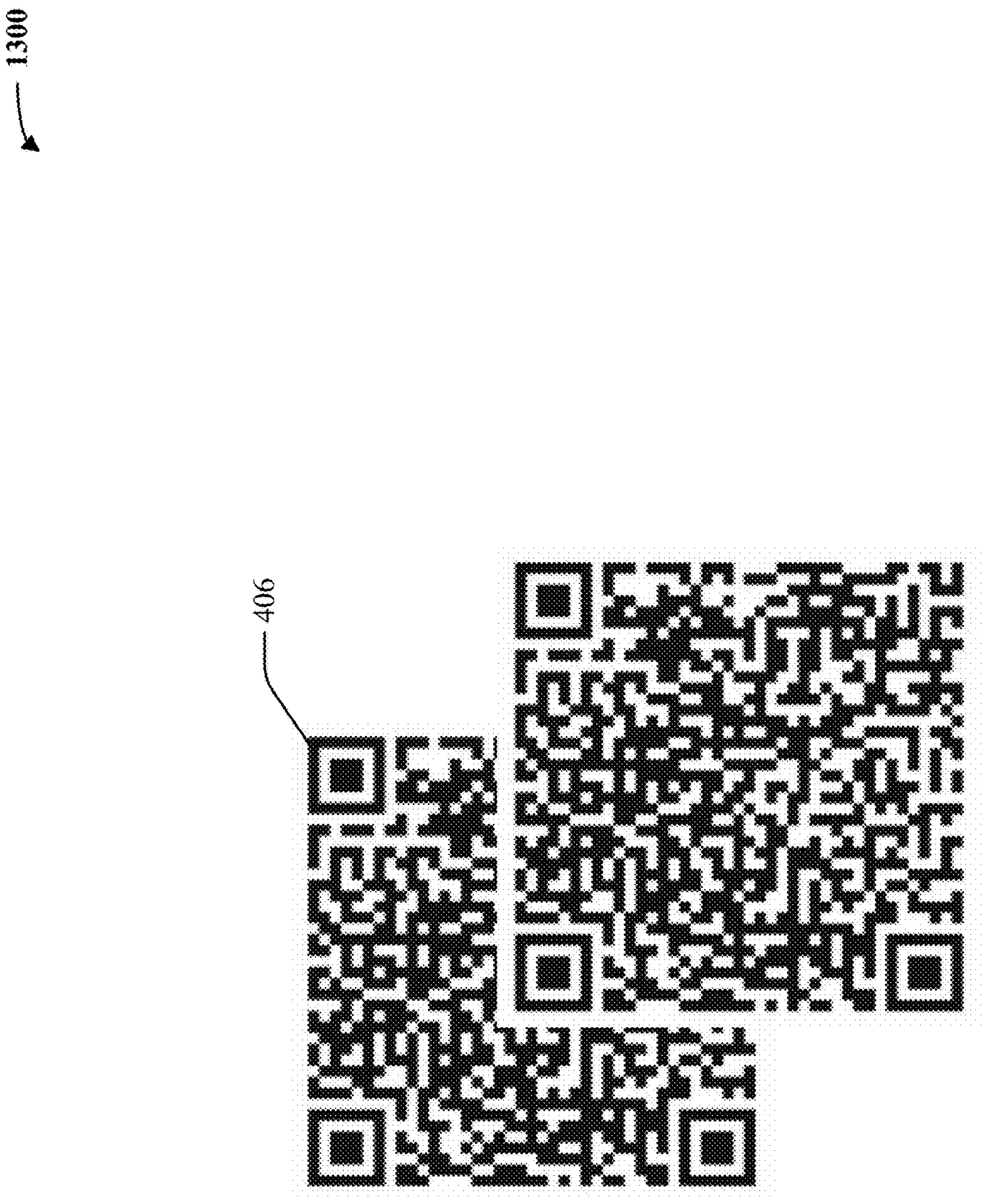
FIG. 13 illustrates a non-limiting example diagram of QR codes for facilitating dynamic system state capture for troubleshooting of medical devices in accordance with one or more embodiments described herein.

FIG. 13 illustrates a non-limiting example diagram 1300 of QR codes for facilitating dynamic system state capture for troubleshooting of medical devices in accordance with one or more embodiments described herein.

Depicted in FIG. 13 is a non-limiting example of one or more QR codes 406 that can be generated by encryption component 118 based on system state digest 210. The one or more QR codes 406 can be displayed on graphical user interface 404 of the electronic display of medical device 104. In some instances, user 402 can interact with graphical user interface 404 (e.g., scroll through pages, click through pages) to view all one or more QR codes 406, so as to view and/or scan the entirety of one or more QR codes 406. In other words, the graphical user interface 404 can visually render, depict, or otherwise illustrate the one or more QR codes 406 on the electronic display.

Figure 14:
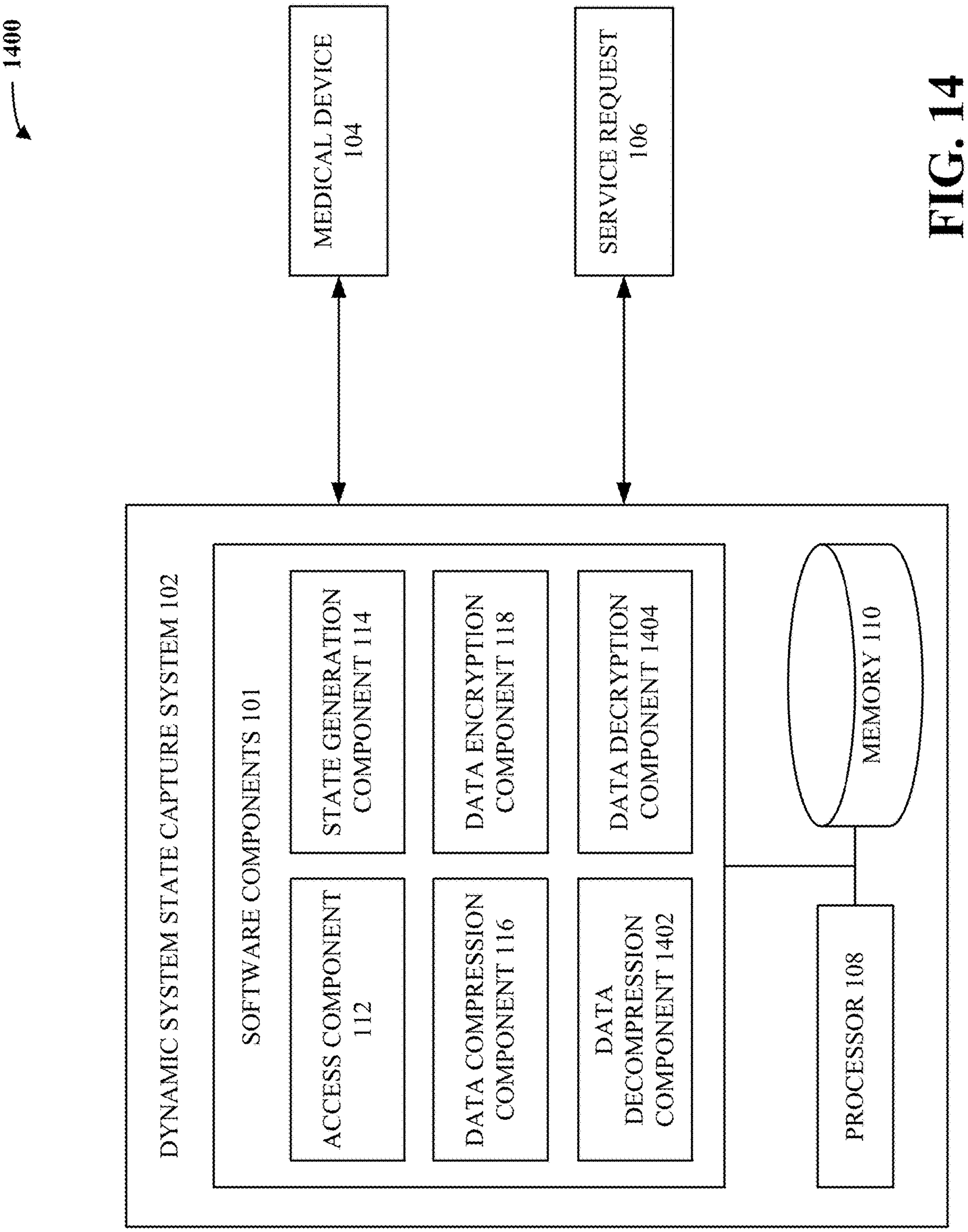
FIG. 14 illustrates a block diagram of an example, non-limiting system including a data decompression component and a data decryption component that facilitates dynamic system state capture for troubleshooting of medical devices in accordance with one or more embodiments described herein.

FIG. 14 illustrates a block diagram of an example, non-limiting system 1400 including a data decompression component and a data decryption component that facilitates dynamic system state capture for troubleshooting of medical devices in accordance with one or more embodiments described herein. As shown, the non-limiting system 1400 can, in some cases, comprise the same components as non-limiting system 100, and can further comprise a data decompression component 1402 and a data decryption component 1404.

Software components 101 can further comprise data decompression component 1402 and data decryption component 1404.

In various aspects, the encryption of the system state digest 210 can be transmitted to the cloud backend 410. In response to the cloud backend 410 receiving the encryption of the system state digest 210, the data decryption component 1404 can decrypt the encryption of the system state digest 210. Following decryption of the system state digest 210, the data decompression component 1402 can decompress the system state digest 210. Non-limiting aspects of decryption and decompression of the system state digest 210 are described with respect to FIGS. 15 and 17.

Figure 15:
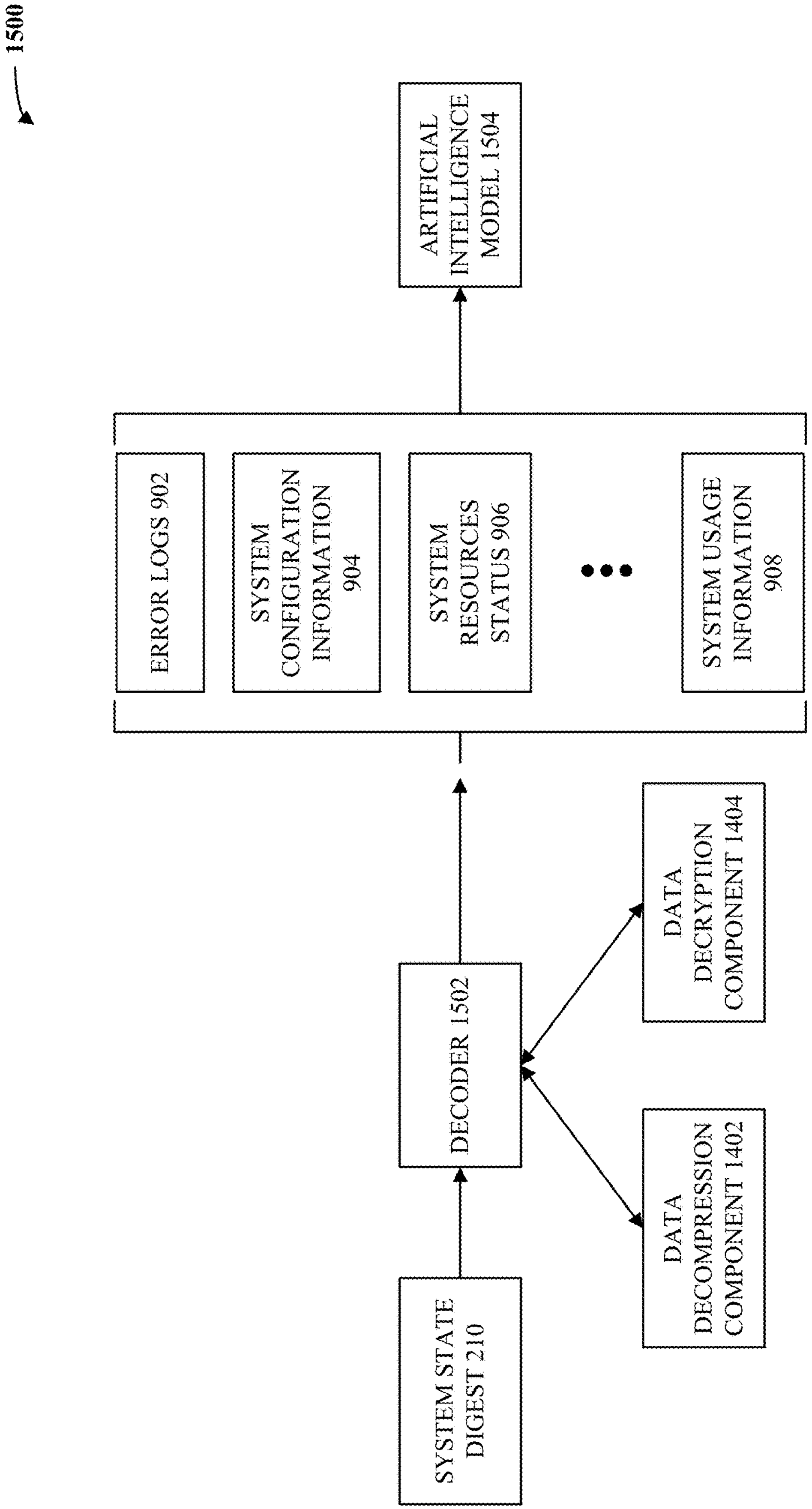
FIG. 15 illustrates a block diagram of an example, non-limiting process of decoding the system state digest for facilitating dynamic system state capture for troubleshooting of medical devices in accordance with one or more embodiments described herein.

FIG. 15 illustrates a block diagram of an example, non-limiting process 1500 of decoding the system state digest for facilitating dynamic system state capture for troubleshooting of medical devices in accordance with one or more embodiments described herein. Decoding the encryption of the system state digest 210 can comprise decrypting the encryption of the system state digest 210, and can further comprise decompressing the system state digest 210. Specifically, the encryption of the system state digest 210 can be received by a decoder 1502. The decoder 1502 can comprise an artificial intelligence model. The artificial intelligence model can comprise or exhibit any suitable internal architecture. For example, the artificial intelligence model can be a deep learning neural network that can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the deep learning neural network can include any suitable numbers of neurons in various layers (e.g., different layers can have the same or different numbers of neurons as each other). As yet another example, the deep learning neural network can include any suitable activation functions (e.g., softmax, sigmoid, hyperbolic tangent, rectified linear unit) in various neurons (e.g., different neurons can have the same or different activation functions as each other). As still another example, the deep learning neural network can include any suitable interneuron connections or interlayer connections (e.g., forward connections, skip connections, recurrent connections).

In some instances, the artificial intelligence model can be a natural language processing (NLP) model. For example, the NLP model's architecture can be designed using various paradigms for processing and understanding language (e.g., recurrent neural networks, transformers, convolutional neural networks). As another example, the NLP model can utilize a sequential architecture where information is processed one element (word) at a time. This could involve recurrent neural networks (RNNs) like Long Short-Term Memory (LSTM) networks which can capture dependencies between words in a sequence. As yet another example, the architecture can leverage transformers for parallel processing of information within a sentence. As still another example, the NLP model can incorporate convolutional neural networks (CNNs) for specific tasks like text classification or named entity recognition.

In other cases, the artificial intelligence model can be an Optical Character Recognition (OCR) model. For example, the OCR model's architecture can leverage various approaches for text decoding (e.g., rule-based systems, statistical language models, deep learning architectures). As another example, the OCR model can be designed with a segmentation stage followed by a recognition stage. The segmentation stage might employ CNNs to isolate individual characters within an image, while the recognition stage could utilize RNNs like LSTM networks to analyze the sequence of characters and predict their most likely identities. As yet another example, the architecture can incorporate attention mechanisms to focus on specific regions of interest within the image during the recognition process. As still another example, the OCR model can be trained with an encoder-decoder architecture, where the encoder processes the image and extracts relevant features, and the decoder utilizes these features along with language models to generate the final text output. The data decompression component 1402 and data decryption component 1404 can electronically store, maintain, control, or otherwise access the decoder 1502 to decrypt and decompress the system state digest 210.

In various cases, if the artificial intelligence model has not yet undergone any training, the training component 208 can randomly initialize the trainable internal parameters (e.g., convolutional kernels, weight matrices, bias vectors) of the deep learning neural network. In contrast, if the artificial intelligence model has already undergone at least some training, the training component 208 can refrain from re-initializing the trainable internal parameters of the artificial intelligence model.

In various aspects, the training component 208 can execute the artificial intelligence model on the encryption of the system state digest 210, thereby causing the artificial intelligence model to produce some output. In particular, the training component 208 can feed the encryption of the system state digest 210 to an input layer of the artificial intelligence model, the encryption of the system state digest 210 can complete a forward pass through one or more hidden layers of the artificial intelligence model, and such forward pass can cause an output layer of the artificial intelligence model to compute the output based on activations provided by the one or more hidden layers.

Note that the format, size, or dimensionality of the output can be controlled or otherwise dictated by the number, arrangement, or sizes of the neurons or of other internal parameters (e.g., convolutional kernels) that are contained in or that otherwise make up the output layer of the artificial intelligence model. So, the output can be forced to have any suitable or any desired format, size, or dimensionality, by adding, removing, or otherwise adjusting neurons or other internal parameters to, from, or within the output layer of the artificial intelligence model. In various cases, if the artificial intelligence model has so far undergone no or little training, the output can be highly inaccurate.

In any case, the training component 208 can compute an error or loss (e.g., mean absolute error (MAE), mean squared error (MSE), cross-entropy error) between the output and a ground truth. In various aspects, the training component 208 can update the trainable internal parameters of the artificial intelligence model by performing backpropagation (e.g., stochastic gradient descent) driven by the computed error or loss.

In various aspects, such training procedure can be repeated for any suitable number of pairs of an encryption of the system state digest 210 and a ground truth. Such training can ultimately cause the trainable internal parameters of the artificial intelligence model to become iteratively optimized for accurately decoding the encryption of the system state digest 210. Note that the training component 208 can implement any suitable training batch sizes, any suitable training termination criteria, or any suitable error, loss, or objective functions.

In response to decrypting and decompressing the system state digest 210, the cloud backend 410 can thus access the system state digest 210 to obtain the troubleshooting data. For instance, the cloud backend 410 can access error logs 1002, system configuration information 1004, system resources status 1006, system usage information 1008, and/or any suitable troubleshooting data relevant to the system failure of the medical device 104 (e.g., troubleshooting data that is known or deemed to solve or address the service request 106 (in the opinion of the artificial intelligence model 206). In various embodiments, the troubleshooting data can be input into an artificial intelligence model 1504. In some embodiments, the data decryption component 1404 can electronically store, maintain, control, or otherwise access the artificial intelligence model 1504.

Figure 16:
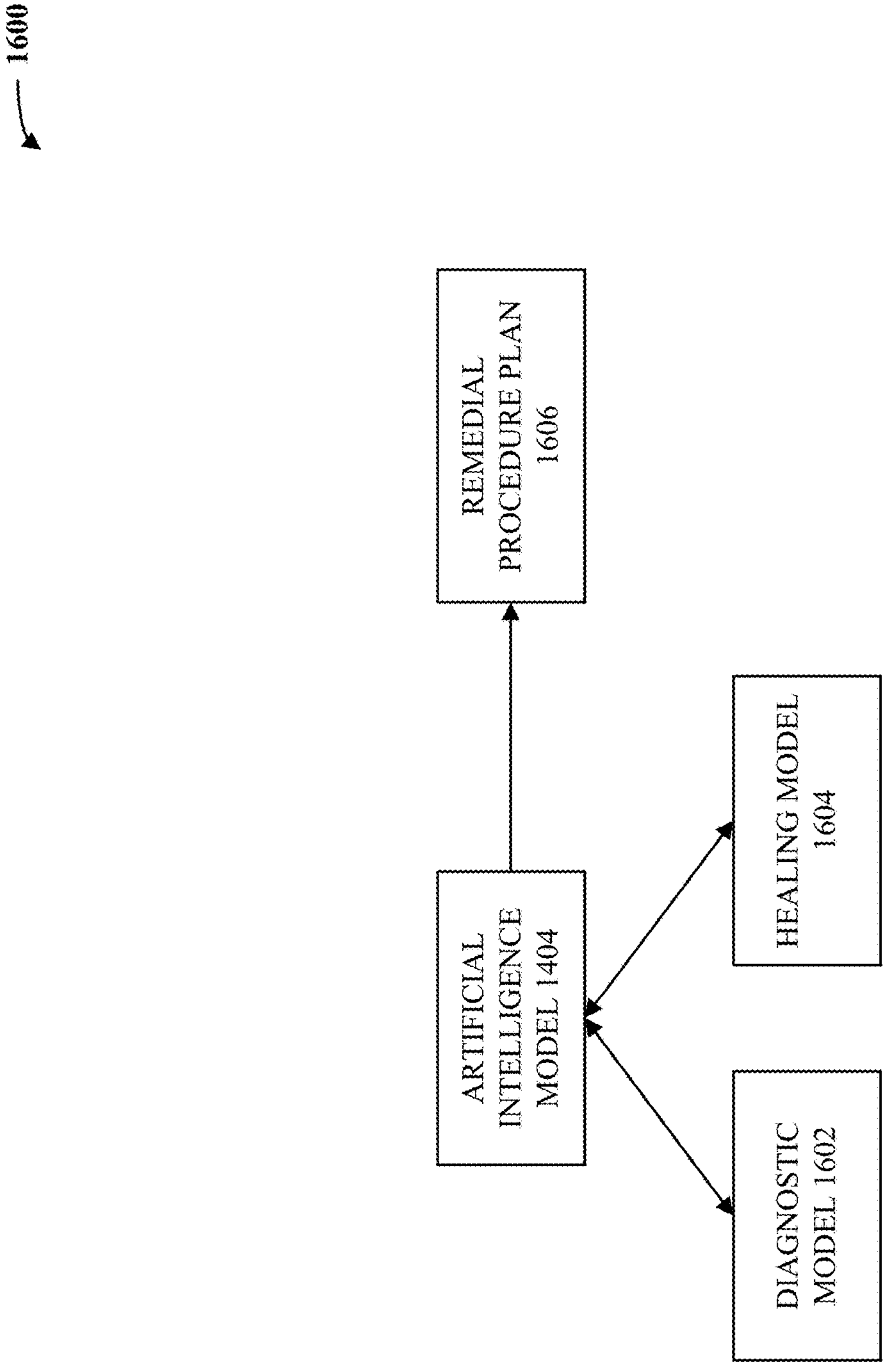
FIG. 16 illustrates a block diagram of an example, non-limiting process of generating a remedial procedure plan for facilitating dynamic system state capture for troubleshooting of medical devices in accordance with one or more embodiments described herein.

FIG. 16 illustrates a block diagram of an example, non-limiting process 1600 of generating a remedial procedure plan for facilitating dynamic system state capture for troubleshooting of medical devices in accordance with one or more embodiments described herein.

In various embodiments, the artificial intelligence model 1504 can comprise one or more sub-models. For instance, the artificial intelligence model 1504 can comprise diagnostic model 1602 and/or healing model 1604. The comprise diagnostic model 1602 and healing model 1604 can exhibit any suitable internal architecture. For example, the diagnostic model 1602 and healing model 1604 can be deep learning neural networks that can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the diagnostic model 1602 and healing model 1604 can include any suitable numbers of neurons in various layers (e.g., different layers can have the same or different numbers of neurons as each other). As yet another example, the diagnostic model 1602 and healing model 1604 can include any suitable activation functions (e.g., softmax, sigmoid, hyperbolic tangent, rectified linear unit) in various neurons (e.g., different neurons can have the same or different activation functions as each other). As still another example, the diagnostic model 1602 and healing model 1604 can include any suitable interneuron connections or interlayer connections (e.g., forward connections, skip connections, recurrent connections). In some instances, the diagnostic model 1602 and healing model 1604 can comprise different or same internal architectures.

In various cases, if the diagnostic model 1602 has not yet undergone any training, the training component 208 can randomly initialize the trainable internal parameters (e.g., convolutional kernels, weight matrices, bias vectors) of the deep learning neural network. In contrast, if the diagnostic model 1602 has already undergone at least some training, the training component 208 can refrain from re-initializing the trainable internal parameters of the diagnostic model 1602.

In various aspects, the training component 208 can execute the diagnostic model 1602 on the troubleshooting data, thereby causing the diagnostic model 1602 to produce some output. In particular, the training component 208 can feed the troubleshooting data to an input layer of the diagnostic model 1602, the troubleshooting data can complete a forward pass through one or more hidden layers of the diagnostic model 1602, and such forward pass can cause an output layer of the diagnostic model 1602 to compute the output based on activations provided by the one or more hidden layers.

Note that the format, size, or dimensionality of the output can be controlled or otherwise dictated by the number, arrangement, or sizes of the neurons or of other internal parameters (e.g., convolutional kernels) that are contained in or that otherwise make up the output layer of the diagnostic model 1602. So, the output can be forced to have any suitable or any desired format, size, or dimensionality, by adding, removing, or otherwise adjusting neurons or other internal parameters to, from, or within the output layer of the diagnostic model 1602. In various cases, if the diagnostic model 1602 has so far undergone no or little training, the output can be highly inaccurate.

In any case, the training component 208 can compute an error or loss (e.g., mean absolute error (MAE), mean squared error (MSE), cross-entropy error) between the output and a ground truth. In various aspects, the training component 208 can update the trainable internal parameters of the diagnostic model 1602 by performing backpropagation (e.g., stochastic gradient descent) driven by the computed error or loss.

In various aspects, such training procedure can be repeated for any suitable number of pairs of troubleshooting data and a ground truth. Such training can ultimately cause the trainable internal parameters of the diagnostic model 1602 to become iteratively optimized for accurately diagnosing the system failure of medical device 104. Note that the training component 208 can implement any suitable training batch sizes, any suitable training termination criteria, or any suitable error, loss, or objective functions.

In various aspects, in response to the artificial intelligence model 1504 receiving troubleshooting data, the troubleshooting data can be input into diagnostic model 1602 so as to produce a diagnosis of the system failure of medical device 104. The diagnosis of the system failure of medical device 104 output by diagnostic model 1602 can comprise any suitable format (e.g., one or more scalars, one or more vectors, one or more matrices, one or more tensors, one or more character strings, or any suitable combination thereof). Accordingly, the diagnosis of the system failure of medical device 104 can be input into healing model 1604.

In various cases, if the healing model 1604 has not yet undergone any training, the training component 208 can randomly initialize the trainable internal parameters (e.g., convolutional kernels, weight matrices, bias vectors) of the deep learning neural network. In contrast, if the healing model 1604 has already undergone at least some training, the training component 208 can refrain from re-initializing the trainable internal parameters of the healing model 1604.

In various aspects, the training component 208 can execute the healing model 1604 on the diagnosis, thereby causing the healing model 1604 to produce some output. In particular, the training component 208 can feed the diagnosis to an input layer of the healing model 1604, the diagnosis can complete a forward pass through one or more hidden layers of the healing model 1604, and such forward pass can cause an output layer of the healing model 1604 to compute the output based on activations provided by the one or more hidden layers.

Note that the format, size, or dimensionality of the output can be controlled or otherwise dictated by the number, arrangement, or sizes of the neurons or of other internal parameters (e.g., convolutional kernels) that are contained in or that otherwise make up the output layer of the healing model 1604. So, the output can be forced to have any suitable or any desired format, size, or dimensionality, by adding, removing, or otherwise adjusting neurons or other internal parameters to, from, or within the output layer of the healing model 1604. In various cases, if the healing model 1604 has so far undergone no or little training, the output can be highly inaccurate.

In any case, the training component 208 can compute an error or loss (e.g., mean absolute error (MAE), mean squared error (MSE), cross-entropy error) between the output and a ground truth. In various aspects, the training component 208 can update the trainable internal parameters of the healing model 1604 by performing backpropagation (e.g., stochastic gradient descent) driven by the computed error or loss.

In various aspects, such training procedure can be repeated for any suitable number of pairs of diagnosis and a ground truth. Such training can ultimately cause the trainable internal parameters of the healing model 1604 to become iteratively optimized for accurately generating a remedial procedure plan to address or resolve the system failure of medical device 104. Note that the training component 208 can implement any suitable training batch sizes, any suitable training termination criteria, or any suitable error, loss, or objective functions.

In various aspects, in response to the diagnostic model 1602 outputting a diagnosis of the system failure of medical device 104, the diagnosis can be input into healing model 1604 so as to produce a remedial procedure plan 1606 for the system failure of medical device 104. The remedial procedure plan 1606 output by diagnostic model 1602 can comprise any suitable electronic format. That is, the remedial procedure plan 1606 can contain video content, text data, AR content, VR content, images, or any suitable combination thereof.

As a non-limiting example, the remedial procedure plan 1606 can contain instructional videos that pertain to resolving the system failure. As another non-limiting example, the remedial procedure plan 1606 can contain a manual or handbook that textually describes how to resolve the system failure. As yet another non-limiting example, the remedial procedure plan 1606 can contain an AR-guided tutorial that overlays step-by-step repair instructions. As still another non-limiting example, the remedial procedure plan 1606 can contain VR simulation that allows the user to practice remediating the system failure on a virtual model of the medical device 104. In any case, the remedial procedure plan 1606 can be transmitted from cloud backend 410 to the medical device 104 or mobile device 408. Thus, graphical user interface 404 can visually render the remedial procedure plan 1606 on the electronic display or mobile device 408, so as to enable user 402 to follow the remedial procedure plan 1606 to resolve the system failure.

In various aspects, any of the artificial intelligence models described herein (e.g., artificial intelligence model 206, artificial intelligence model 1404, diagnostic model 1602, healing model 1604) can undergo any suitable training methods (e.g., unsupervised training, supervised training).

Figure 17:
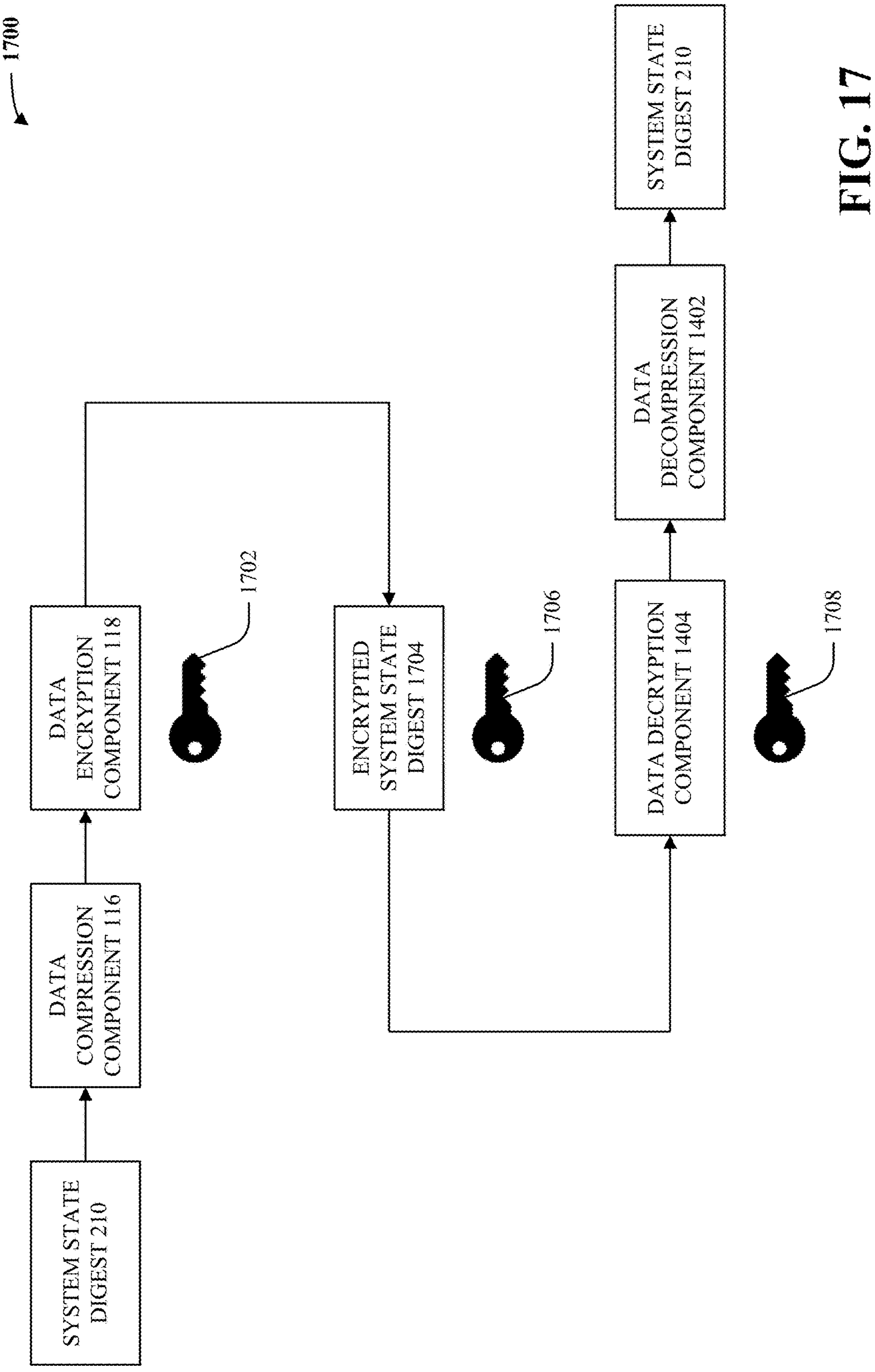
FIG. 17 illustrates a block diagram of an example, non-limiting process of encrypting and decrypting the system state digest for facilitating dynamic system state capture for troubleshooting of medical devices in accordance with one or more embodiments described herein.

FIG. 17 illustrates a block diagram of an example, non-limiting process 1700 of encrypting and decrypting the system state digest for facilitating dynamic system state capture for troubleshooting of medical devices in accordance with one or more embodiments described herein.

In various embodiments, the data compression component 116 can compress the system state digest 210. As a non-limiting example, the data compression component 116 can compress the system state digest 210 using GNU zip (gzip). The compressed system state digest 210 can then be input into data encryption component 118 to produce an encrypted system state digest 1506. In various aspects, data encryption component 118 can generate a random symmetric key. The data encryption component 118 can encrypt the compressed system state digest 210 with the random symmetric key. In various embodiments, data encryption component 118 can encrypt the random symmetric key with a public key 1702. The random symmetric key encrypted with a public key 1702 can be referred to as encrypted random symmetric key 1706.

In various instances, the encrypted system state digest 1506 can be converted into one or more QR codes 406 or encoded text 1102 by data encryption component 118 for offline transfer via mobile device 408. In other cases, the encrypted system state digest 1506 can be transmitted to cloud backend 410 as is.

In various embodiments, the cloud backend 410 can receive the encrypted system state digest 1506 (e.g., as is, as one or more QR codes 406, as encoded text 1102) and the encrypted random symmetric key 1706. If the cloud backend 410 receives one or more QR codes 406, the data decryption component 1404 and data decompression component 1402 can decrypt and decompress the encrypted system state digest 1506 into a plain text format.

In various embodiments, the data decryption component 1404 can receive the encrypted system state digest 1506 and encrypted random symmetric key 1706. Accordingly, the data decryption component 1404 can decrypt the 1404 can receive the encrypted system state digest 1506 and encrypted with a private key 1708. Thus, data decryption component 1404 can then decrypt the encrypted system state digest 1506 with the random symmetric key.

Once decrypted, the data decompression component 1402 can decompress the decrypted system state digest 210 using gzip to obtain the system state digest 210.

Figure 18:
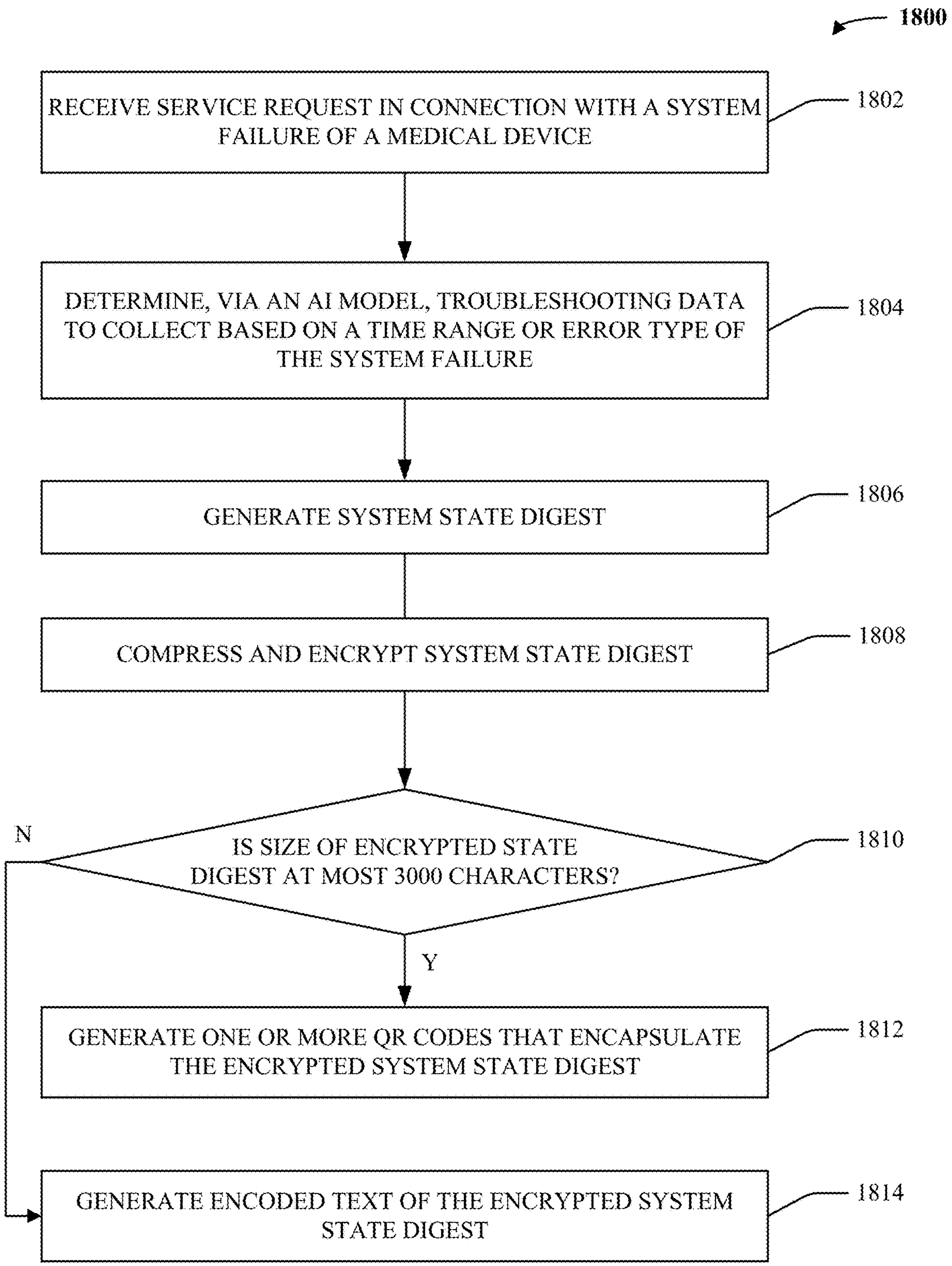
FIG. 18 illustrates a flow diagram of an example, non-limiting computer-implemented method that facilitates dynamic system state capture for troubleshooting of medical devices in accordance with one or more embodiments described herein.

FIG. 18 illustrates a flow diagram of an example, non-limiting computer-implemented method 1800 that facilitates dynamic system state capture for troubleshooting of medical devices in accordance with one or more embodiments described herein.

In various embodiments, act 1802 can include receiving, by a device (e.g., via 112) operatively coupled to a processor (e.g., 108), a service request (e.g., 106) in connection with a system failure of a medical device (e.g., 104).

In various aspects, act 1804 can include determining, by the device (e.g., via 112) and via an artificial intelligence model (e.g., 206), troubleshooting data to collect based on a time range (e.g., 202) and/or error type (e.g., 204) of the system failure.

Although not explicitly shown in FIG. 18, the computer-implemented method 1800 can comprise: training, by the device (e.g., via 208), the artificial intelligence model and deploying the artificial intelligence model after training.

In various instances, act 1806 can include generating, by the device (e.g., via 114), a system state digest (e.g., 210).

In various cases, act 1808 can include compressing, by the device (e.g., via 116) and encrypting, by the device (e.g., via 118), the system state digest.

In various cases, act 1810 can include determining if the size of the encrypted state digest is at most 3000 characters. If yes (e.g., the size of the encrypted state digest is at most 3000 characters), the non-limiting computer-implemented method 1800 can proceed to act 1812. If no (e.g., the size of the encrypted state digest is not at most 3000 characters), the non-limiting computer-implemented method 1800 can proceed to act 1814.

In various cases, act 1812 can include generating, by the device (e.g., via 116) one or more QR codes (e.g., 406) that encapsulate the encrypted system state digest.

In various cases, act 1814 can include generating, by the device (e.g., via 116) encoded text (e.g., 1102) of the encrypted system state digest.

Figure 19:
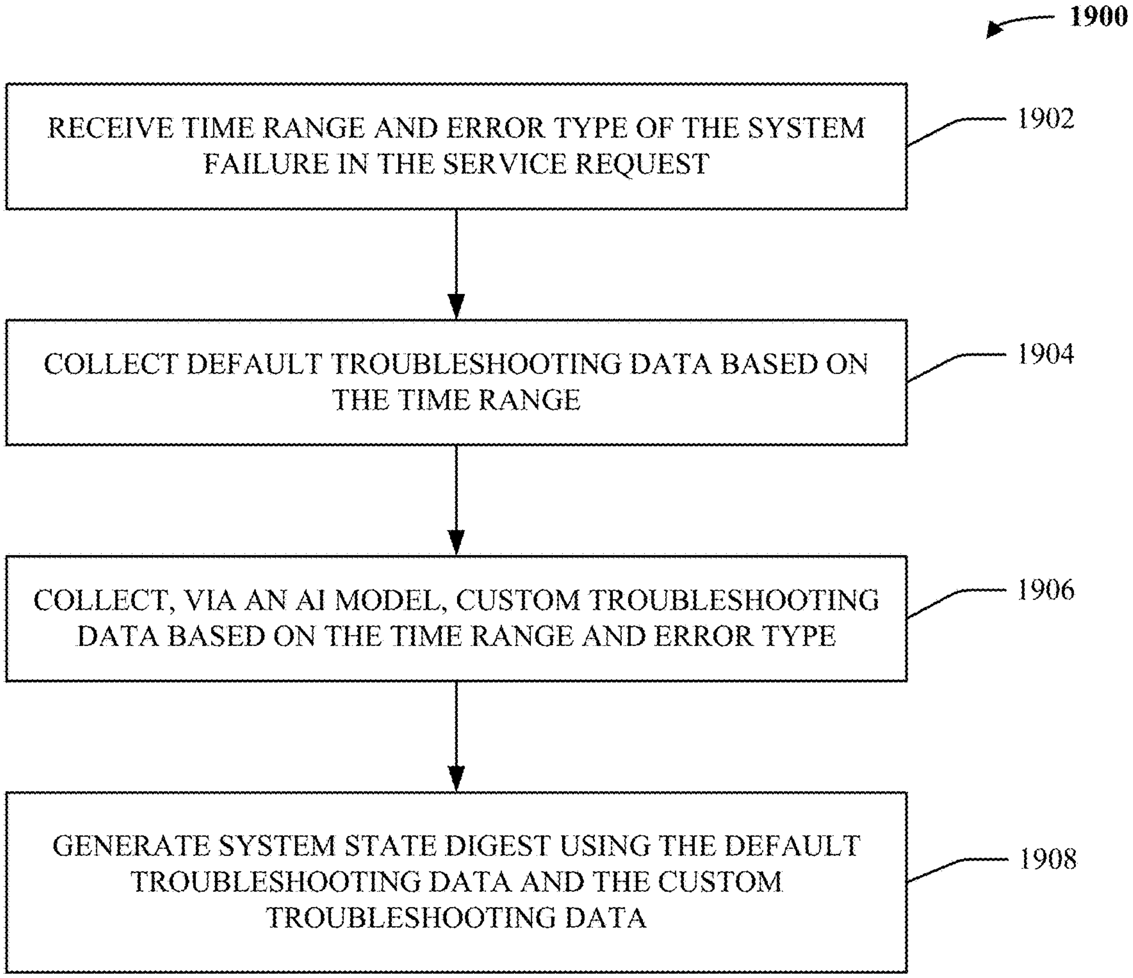
FIG. 19 illustrates a flow diagram of an example, non-limiting computer-implemented method that facilitates dynamic system state capture for troubleshooting of medical devices in accordance with one or more embodiments described herein.

FIG. 19 illustrates a flow diagram of an example, non-limiting computer-implemented method 1900 that facilitates dynamic system state capture for troubleshooting of medical devices in accordance with one or more embodiments described herein.

In various embodiments, act 1902 can include receiving, by a device (e.g., via 112) operatively coupled to a processor (e.g., 108), the time range and/or error type of the system failure in the service request.

In various aspects, act 1904 can include collecting, by the device (e.g., via 112), default troubleshooting data based on the time range.

In various instances, act 1906 can include collecting, by the device (e.g., via 112) and via the artificial intelligence model, custom troubleshooting data based on the time range and error type. Note that, the access component 112 can collect the default troubleshooting data and custom troubleshooting data in any order or sequence (e.g., collect default troubleshooting data before custom troubleshooting data, collect default troubleshooting data after custom troubleshooting data, collect default troubleshooting data and custom troubleshooting data in parallel).

In various cases, act 1908 can include generating, by the device (e.g., via 114), the system state digest using the default troubleshooting data and custom troubleshooting data.

Figure 20:
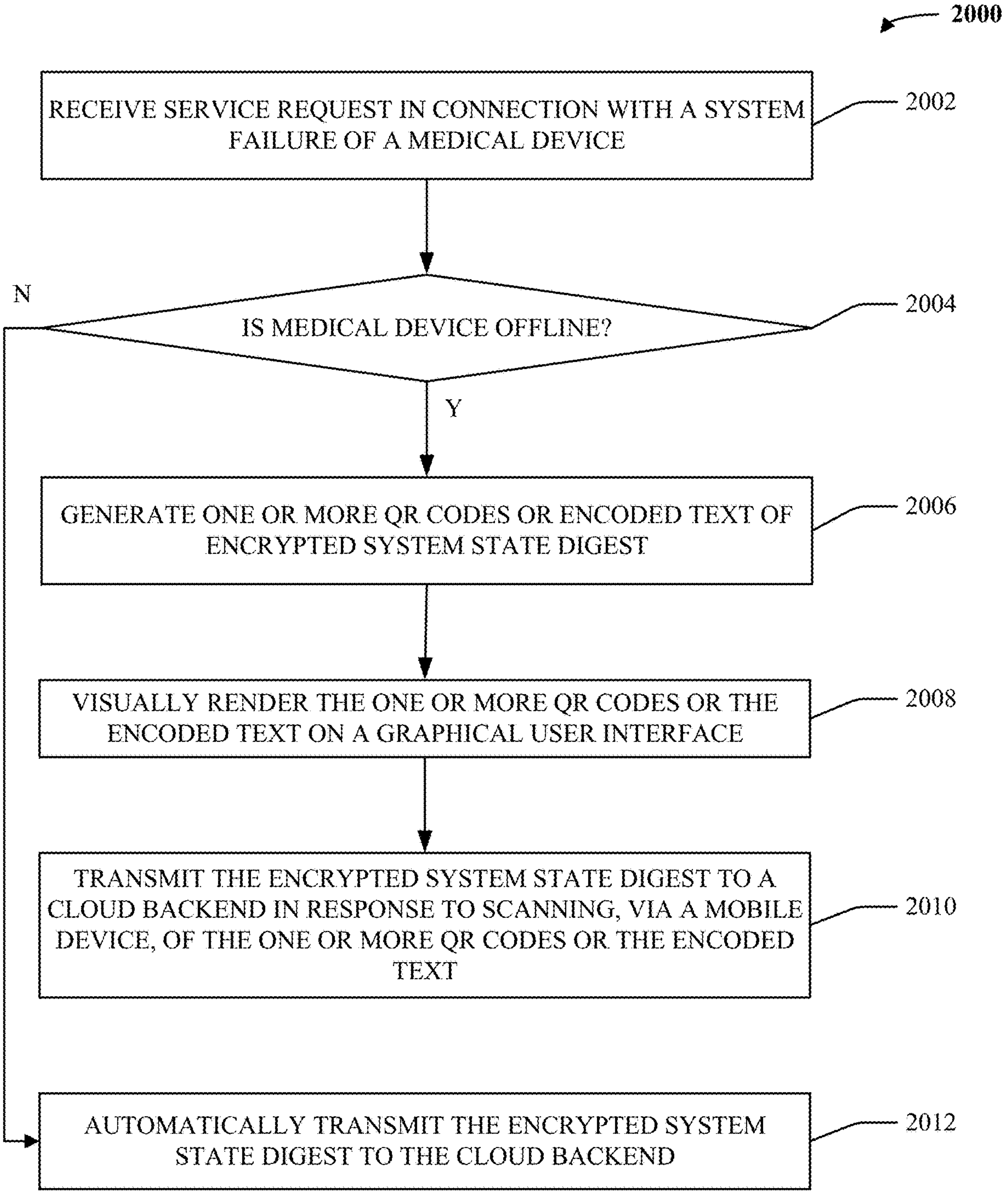
FIG. 20 illustrates a flow diagram of an example, non-limiting computer-implemented method that facilitates dynamic system state capture for troubleshooting of medical devices in accordance with one or more embodiments described herein.

FIG. 20 illustrates a flow diagram of an example, non-limiting computer-implemented method 2000 that facilitates dynamic system state capture for troubleshooting of medical devices in accordance with one or more embodiments described herein.

In various embodiments, act 2002 can include receiving, by a device (e.g., via 112) operatively coupled to a processor (e.g., 108), a service request (e.g., 106) in connection with a system failure of a medical device (e.g., 104).

In various cases, act 2004 can include determining if the medical device is offline. If yes (e.g., the medical device is offline), the non-limiting computer-implemented method 2000 can proceed to act 2006. If no (e.g., the medical device is online), the non-limiting computer-implemented method 2000 can proceed to act 2012.

In various cases, act 2006 can include generating, by the device (e.g., via 116) one or more QR codes or encoded text of the encrypted system state digest.

In various cases, act 2008 can include visually rendering, by the device (e.g., via 212) the one or more QR codes or the encoded text on a graphical user interface (e.g., 304).

In various cases, act 2010 can include transmitting, by the device (e.g., via 410), the encrypted system state digest to the cloud backend in response to scanning, via a mobile device (e.g., 308) of the one or more QR codes or the encoded text.

In various cases, act 2012 can include automatically transmitting, by the device (e.g., via 118), the encrypted system state digest to the cloud backend.

Figure 21:
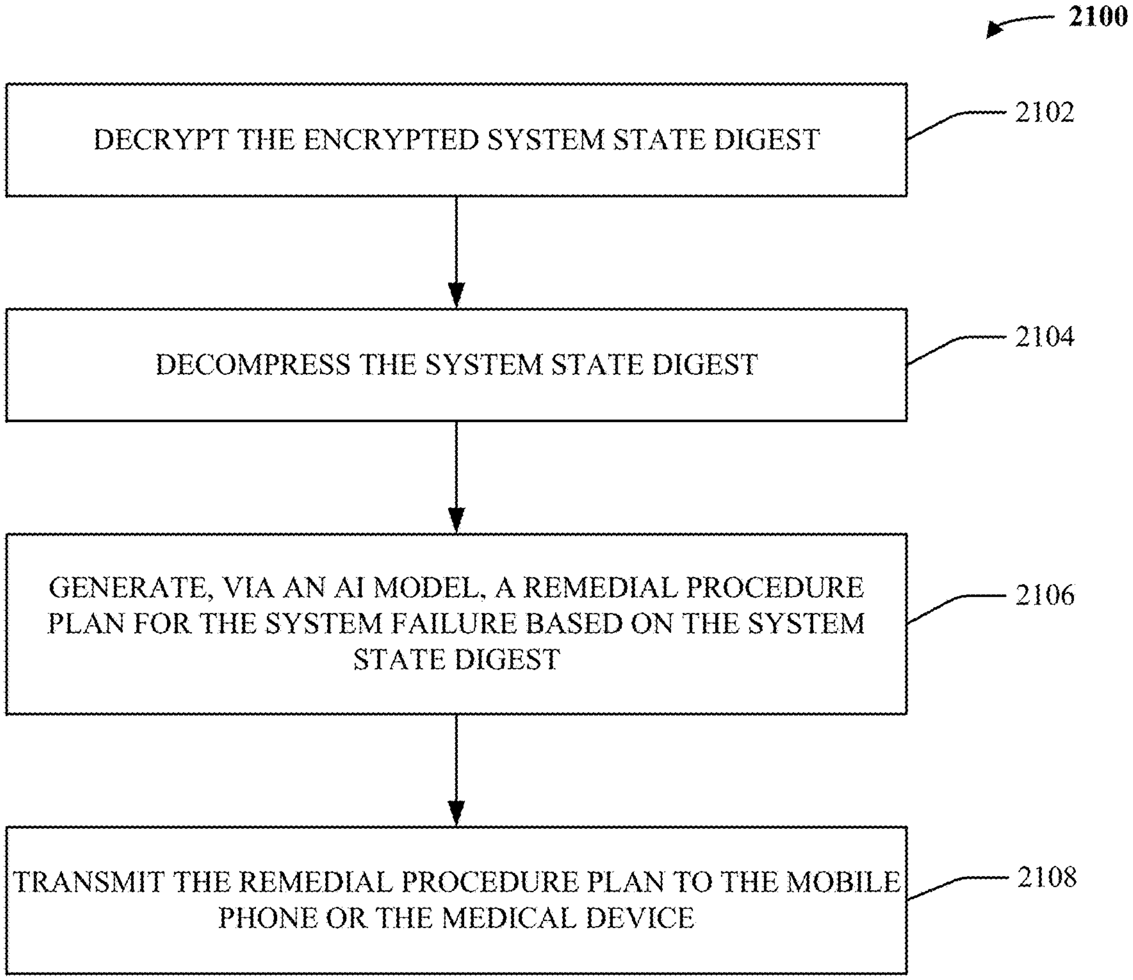
FIG. 21 illustrates a flow diagram of an example, non-limiting computer-implemented method that facilitates dynamic system state capture for troubleshooting of medical devices in accordance with one or more embodiments described herein.

FIG. 21 illustrates a flow diagram of an example, non-limiting computer-implemented method 2100 that can facilitate dynamic system state capture for troubleshooting of medical devices in accordance with one or more embodiments described herein. In various cases, the dynamic system state capture system 102 can facilitate the computer-implemented method 2100.

In various embodiments, act 2102 can include decrypting, by a device (e.g., via 410) operatively coupled to a processor (e.g., 108), the encrypted system state digest.

In various aspects, act 2104 can include decompressing, by the device (e.g., via 410), the system state digest.

In various instances, act 2106 can include generating, by the device (e.g., via 410) and via an artificial intelligence model, a remedial procedure plan for the system failure based on the system state digest.

In various cases, act 2108 can include transmitting, by the device (e.g., via 410), the remedial procedure plan to the mobile phone or the medical device.

Thus far, various embodiments have been described with respect to troubleshooting of medical devices. However, this is a mere non-limiting example. In various aspects, various embodiments described can be applied or otherwise extrapolated to any suitable machines (e.g., machines that are not medical devices).

The systems and/or devices have been (and/or will be further) described herein with respect to interaction between one or more components. Such systems and/or components can include those components or sub-components specified therein, one or more of the specified components and/or sub-components, and/or additional components. Sub-components can be implemented as components communicatively coupled to other components rather than included within parent components. One or more components and/or sub-components can be combined into a single component providing aggregate functionality. The components can interact with one or more other components not specifically described herein for the sake of brevity, but known by those of skill in the art.

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by f(z)=confidence(class). Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

Figure 23:
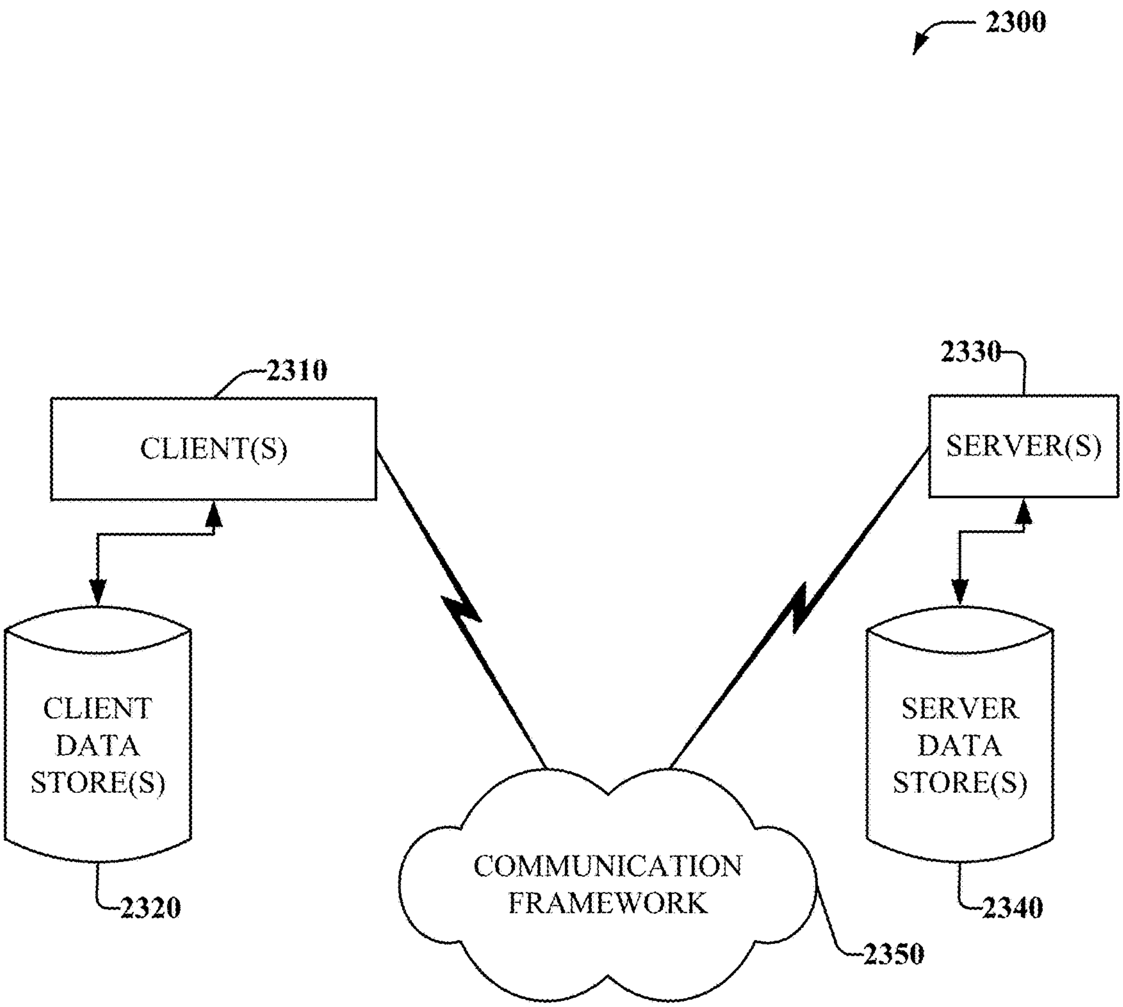
FIG. 23 illustrates an example networking environment operable to execute various implementations described herein.

In order to provide additional context for various embodiments described herein, FIG. 23 and the following discussion are intended to provide a brief, general description of a suitable computing environment 2300 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

Figure 22:
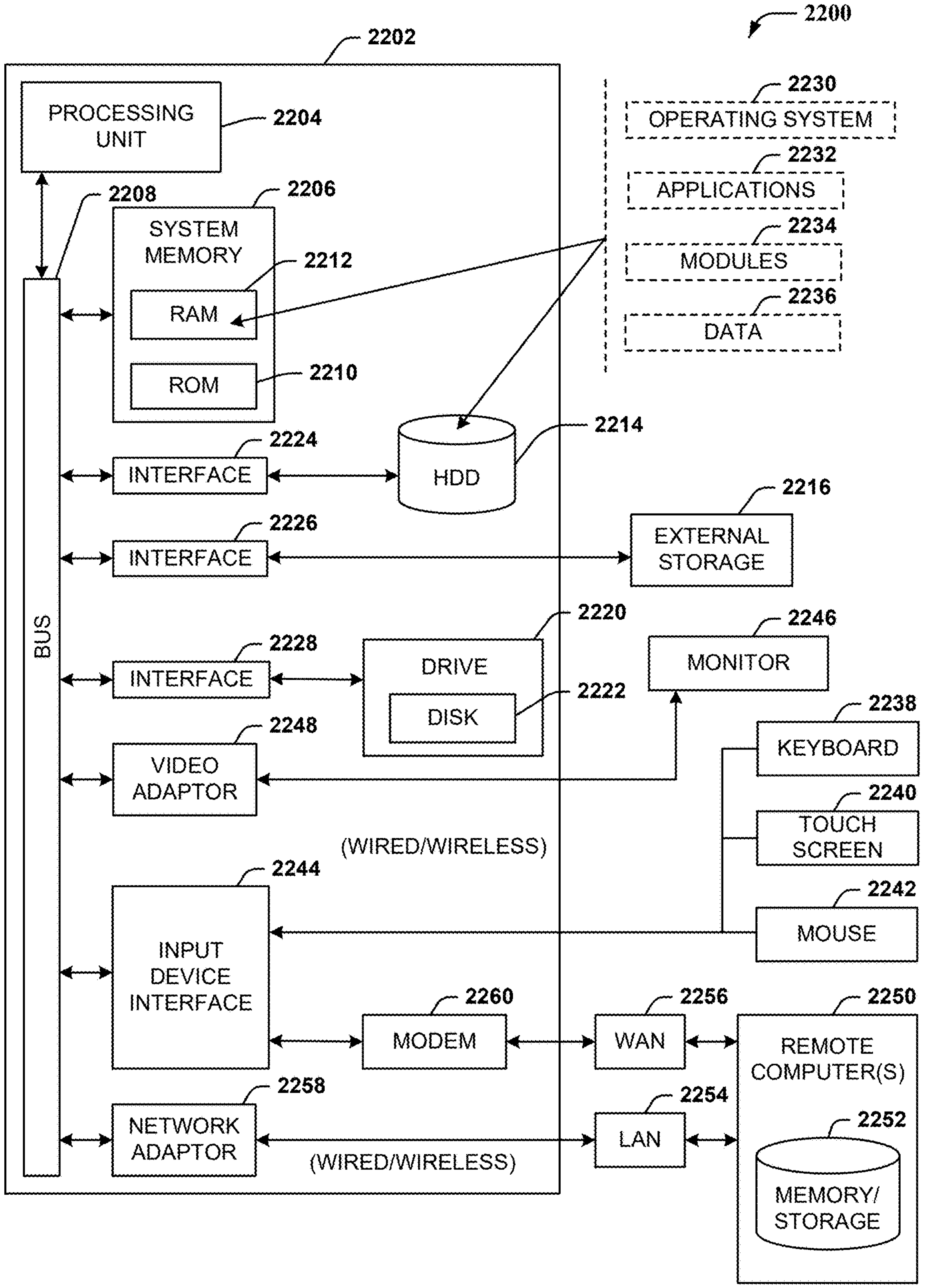
FIG. 22 illustrates a block diagram of an example, non-limiting operating environment in which one or more embodiments described herein can be facilitated.

With reference again to FIG. 22, the example environment 2200 for implementing various embodiments of the aspects described herein includes a computer 2202, the computer 2202 including a processing unit 2204, a system memory 2206 and a system bus 2208. The system bus 2208 couples system components including, but not limited to, the system memory 2206 to the processing unit 2204. The processing unit 2204 can be any of various commercially available processors. Dual microprocessors and other multi-processor architectures can also be employed as the processing unit 2204.

The system bus 2208 can be any of several types of bus structure that can further interconnect to a memory bus (with or without a memory controller), a peripheral bus, and a local bus using any of a variety of commercially available bus architectures. The system memory 2206 includes ROM 2210 and RAM 2212. A basic input/output system (BIOS) can be stored in a non-volatile memory such as ROM, erasable programmable read only memory (EPROM), EEPROM, which BIOS contains the basic routines that help to transfer information between elements within the computer 2202, such as during startup. The RAM 2212 can also include a high-speed RAM such as static RAM for caching data.

The computer 2202 further includes an internal hard disk drive (HDD) 2214 (e.g., EIDE, SATA), one or more external storage devices 2216 (e.g., a magnetic floppy disk drive (FDD) 2216, a memory stick or flash drive reader, a memory card reader, etc.) and a drive 2220, e.g., such as a solid state drive, an optical disk drive, which can read or write from a disk 2222, such as a CD-ROM disc, a DVD, a BD, etc. Alternatively, where a solid state drive is involved, disk 2222 would not be included, unless separate. While the internal HDD 2214 is illustrated as located within the computer 2202, the internal HDD 2214 can also be configured for external use in a suitable chassis (not shown). Additionally, while not shown in environment 2200, a solid state drive (SSD) could be used in addition to, or in place of, an HDD 2214. The HDD 2214, external storage device(s) 2216 and drive 2220 can be connected to the system bus 2208 by an HDD interface 2224, an external storage interface 2226 and a drive interface 2228, respectively. The interface 2224 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2212, including an operating system 2230, one or more application programs 2232, other program modules 2234 and program data 2236. All or portions of the operating system, applications, modules, or data can also be cached in the RAM 2212. The systems and methods described herein can be implemented utilizing various commercially available operating systems or combinations of operating systems.

Computer 2202 can optionally comprise emulation technologies. For example, a hypervisor (not shown) or other intermediary can emulate a hardware environment for operating system 2230, and the emulated hardware can optionally be different from the hardware illustrated in FIG. 20. In such an embodiment, operating system 2230 can comprise one virtual machine (VM) of multiple VMs hosted at computer 2202. Furthermore, operating system 2230 can provide runtime environments, such as the Java runtime environment or the .NET framework, for applications 2232. Runtime environments are consistent execution environments that allow applications 2232 to run on any operating system that includes the runtime environment. Similarly, operating system 2230 can support containers, and applications 2232 can be in the form of containers, which are lightweight, standalone, executable packages of software that include, e.g., code, runtime, system tools, system libraries and settings for an application.

Further, computer 2202 can be enable with a security module, such as a trusted processing module (TPM). For instance with a TPM, boot components hash next in time boot components, and wait for a match of results to secured values, before loading a next boot component. This process can take place at any layer in the code execution stack of computer 2202, e.g., applied at the application execution level or at the operating system (OS) kernel level, thereby enabling security at any level of code execution.

A user can enter commands and information into the computer 2202 through one or more wired/wireless input devices, e.g., a keyboard 2238, a touch screen 2240, and a pointing device, such as a mouse 2242. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2204 through an input device interface 2244 that can be coupled to the system bus 2208, but can be connected by other interfaces, such as a parallel port, an IEEE 1394 serial port, a game port, a USB port, an IR interface, a BLUETOOTH® interface, etc.

A monitor 2246 or other type of display device can be also connected to the system bus 2208 via an interface, such as a video adapter 2248. In addition to the monitor 2246, a computer typically includes other peripheral output devices (not shown), such as speakers, printers, etc.

The computer 2202 can operate in a networked environment using logical connections via wired or wireless communications to one or more remote computers, such as a remote computer(s) 2250. The remote computer(s) 2250 can be a workstation, a server computer, a router, a personal computer, portable computer, microprocessor-based entertainment appliance, a peer device or other common network node, and typically includes many or all of the elements described relative to the computer 2202, although, for purposes of brevity, only a memory/storage device 2252 is illustrated. The logical connections depicted include wired/wireless connectivity to a local area network (LAN) 2254 or larger networks, e.g., a wide area network (WAN) 2256. Such LAN and WAN networking environments are commonplace in offices and companies, and facilitate enterprise-wide computer networks, such as intranets, all of which can connect to a global communications network, e.g., the Internet.

When used in a LAN networking environment, the computer 2202 can be connected to the local network 2254 through a wired or wireless communication network interface or adapter 2258. The adapter 2258 can facilitate wired or wireless communication to the LAN 2254, which can also include a wireless access point (AP) disposed thereon for communicating with the adapter 2258 in a wireless mode.

When used in a WAN networking environment, the computer 2202 can include a modem 2260 or can be connected to a communications server on the WAN 2256 via other means for establishing communications over the WAN 2256, such as by way of the Internet. The modem 2260, which can be internal or external and a wired or wireless device, can be connected to the system bus 2208 via the input device interface 2244. In a networked environment, program modules depicted relative to the computer 2202 or portions thereof, can be stored in the remote memory/storage device 2252. It will be appreciated that the network connections shown are example and other means of establishing a communications link between the computers can be used.

When used in either a LAN or WAN networking environment, the computer 2202 can access cloud storage systems or other network-based storage systems in addition to, or in place of, external storage devices 2216 as described above, such as but not limited to a network virtual machine providing one or more aspects of storage or processing of information. Generally, a connection between the computer 2202 and a cloud storage system can be established over a LAN 2254 or WAN 2256 e.g., by the adapter 2258 or modem 2260, respectively. Upon connecting the computer 2202 to an associated cloud storage system, the external storage interface 2226 can, with the aid of the adapter 2258 or modem 2260, manage storage provided by the cloud storage system as it would other types of external storage. For instance, the external storage interface 2226 can be configured to provide access to cloud storage sources as if those sources were physically connected to the computer 2202.

The computer 2202 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

FIG. 23 is a schematic block diagram of a sample computing environment 2300 with which the disclosed subject matter can interact. The sample computing environment 2300 includes one or more client(s) 2310. The client(s) 2310 can be hardware or software (e.g., threads, processes, computing devices). The sample computing environment 2300 also includes one or more server(s) 2330. The server(s) 2330 can also be hardware or software (e.g., threads, processes, computing devices). The servers 2330 can house threads to perform transformations by employing one or more embodiments as described herein, for example. One possible communication between a client 2310 and a server 2330 can be in the form of a data packet adapted to be transmitted between two or more computer processes. The sample computing environment 2300 includes a communication framework 2350 that can be employed to facilitate communications between the client(s) 2310 and the server(s) 2330. The client(s) 2310 are operably connected to one or more client data store(s) 2320 that can be employed to store information local to the client(s) 2310. Similarly, the server (s) 2330 are operably connected to one or more server data store(s) 2340 that can be employed to store information local to the servers 2330.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc.

that perform particular tasks or implement particular abstract data types. Moreover, those skilled in the art will appreciate that various aspects can be practiced with other computer system configurations, including single-processor or multi-processor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A system, comprising:
- a memory that stores computer executable components; and
- a processor that executes at least one of the computer executable components that:
  - collect, in response to a service request in connection with a system failure of a medical device and via an artificial intelligence model, troubleshooting data based on a time range or an error type of the system failure, wherein the time range identifies an interval before and after an occurrence of an error indicator of the system failure, and wherein the artificial intelligence model is trained using mappings between error indicators and troubleshooting data sources;
  - generate a system state digest of the troubleshooting data, wherein the system state digest comprises a compressed and structured representation of the troubleshooting data including system configuration data, system resource data, system usage data, system error data, or a combination thereof, corresponding to the system failure; and
  - dynamically generate an encryption of the system state digest, wherein dynamically generating the encryption comprises performing cryptographic processing by the processor to generate an encrypted system state digest configured for machine-readable transmission from the medical device when the medical device is offline.

2. The system of claim 1, wherein dynamically generating the encryption of the system state digest comprises:
- generating one or more quick response (QR) codes that encapsulates the system state digest in response to the system state digest comprising at most 3000 characters; or
- generating encoded text of the system state digest in response to the system state digest comprising at least 3000 characters.

3. The system of claim 2, wherein generating the one or more QR codes or the encoded text comprises:
- compressing the system state digest; and
- encrypting the system state digest.

4. The system of claim 2, wherein how many of the one or more QR codes are generated is based on a size of the system state digest.

5. The system of claim 1, wherein the at least one of the computer executable components further:
- receive input about the time range or the error type of the system failure in the service request, wherein the input comprises natural language text or audio data.

6. The system of claim 2, wherein the at least one of the computer executable components further:
- transmit the encryption of the system state digest to a cloud backend, wherein transmitting the encryption comprises:
  - automatically transmitting the encryption of the system state digest to the cloud backend in response to the medical device being online; or
  - visually rendering, on a graphical user interface of the medical device, the one or more QR codes or the encoded text in response to the medical device being offline; and
  - transmitting, via scanning the one or more QR codes or the encoded text via a mobile device, the encryption of the system state digest to the cloud backend.

7. The system of claim 6, wherein the at least one of the computer executable components further:
- decrypt the encryption of the system state digest; and
- decompress the system state digest.

8. The system of claim 7, wherein the at least one of the computer executable components further:
- generate, in response to decrypting the system state digest and via a second artificial intelligence model, a remedial procedure plan for the system failure in the service request based on the system state digest.

9. The system of claim 8, wherein the remedial procedure plan comprises text data, video data, image data, augmented reality data, or virtual reality data.

10. The system of claim 8, wherein the at least one of the computer executable components further:
- transmit the remedial procedure plan to the mobile device or the medical device; and
- visually render, on the graphical user interface of the medical device or a graphical user interface of the mobile device, the remedial procedure plan.

11. The system of claim 1, wherein the at least one of the computer executable components further:
- train the artificial intelligence model on knowledge graphs to identify which troubleshooting data to collect, wherein the knowledge graphs comprise mappings between error codes and one or more attributes, and wherein the one or more attributes comprise files, corresponding subsystem components, or topics of the error codes.

12. A computer-implemented method, comprising:
- collecting, by a system operatively coupled to a processor and in response to a service request in connection with a system failure of a medical device, troubleshooting data based on a time range or an error type of the system failure via an artificial intelligence model, wherein the time range identifies an interval before and after an occurrence of an error indicator of the system failure, and wherein the artificial intelligence model is trained using mappings between error indicators and troubleshooting data sources;
- generating, by the system, a system state digest of the troubleshooting data, wherein the system state digest comprises a compressed and structured representation of the troubleshooting data including system configuration data, system resource data, system usage data, system error data, or a combination thereof, corresponding to the system failure; and dynamically generating, by the system, an encryption of the system state digest, wherein dynamically generating the encryption comprises performing cryptographic processing by the processor to generate an encrypted system state digest configured for machine-readable transmission from the medical device when the medical device is offline.

13. The computer-implemented method of claim 12, wherein dynamically generating the encryption of the system state digest comprises:

generating one or more quick response (QR) codes that encapsulates the system state digest in response to the system state digest comprising at most 3000 characters; or generating encoded text of the system state digest in response to the system state digest comprising at least 3000 characters.

14. The computer-implemented method of claim 13, wherein generating the one or more QR codes or the encoded text comprises:

compressing the system state digest; and encrypting the system state digest.

15. The computer-implemented method of claim 13, further comprising:

visually rendering, by the system and on a graphical user interface, the one or more QR codes or the encoded text; and transmits, by the system and via scanning the one or more QR codes or the encoded text via a mobile device, the encryption of the system state digest to a cloud backend.

16. The computer-implemented method of claim 12, further comprising:

decrypting, by the system, the encryption of the system state digest; and decompressing, by the system, the system state digest.

17. The computer-implemented method of claim 12, further comprising:

generating, by the system and in response to decrypting the system state digest, a remedial procedure plan for the system failure in the service request based on the system state digest via a second artificial intelligence model.

18. A computer program product for precision diagnostics and troubleshooting of medical devices, the computer program product comprising a non-transitory computer readable storage medium having program instructions embodied therewith, the program instructions executable by a processor to cause the processor to:

collect, by the processor and in response to a service request in connection with a system failure of a medical device, troubleshooting data based on a time range or an error type of the system failure via an artificial intelligence model, wherein the time range identifies an interval before and after an occurrence of an error indicator of the system failure, and wherein the artificial intelligence model is trained using mappings between error indicators and troubleshooting data sources;

generate, by the processor, a system state digest of the troubleshooting data, wherein the system state digest comprises a compressed and structured representation of the troubleshooting data including system configuration data, system resource data, system usage data, system error data, or a combination thereof, corresponding to the system failure; and dynamically generate, by the processor, an encryption of the system state digest, wherein dynamically generating the encryption comprises performing cryptographic processing by the processor to generate an encrypted system state digest configured for machine-readable transmission from the medical device when the medical device is offline.

19. The computer program product of claim 18, wherein dynamically generating the encryption of the system state digest comprises:

generating one or more quick response (QR) codes that encapsulates the system state digest in response to the system state digest comprising at most 3000 characters; or generating encoded text of the system state digest in response to the system state digest comprising at least 3000 characters.

* * * * *